United States Patent
Gammie et al.

(10) Patent No.: US 11,523,808 B2
(45) Date of Patent: Dec. 13, 2022

(54) DEVICE AND METHOD FOR TRANSSEPTAL PUNCTURE

(71) Applicants: University of Maryland, Baltimore, Baltimore, MD (US); University of Maryland Medical Center, LLC, Baltimore, MD (US)

(72) Inventors: James S. Gammie, Stevenson, MD (US); Rachael Quinn, Abingdon, MD (US); Chetan Pasrija, Baltimore, MD (US)

(73) Assignees: University of Maryland, Baltimore, Baltimore, MD (US); University of Maryland Medical Center, LLC, Baltimore, MD (US)

( * ) Notice: Subject to any disclaimer, the term of this patent is extended or adjusted under 35 U.S.C. 154(b) by 207 days.

(21) Appl. No.: 16/577,345

(22) Filed: Sep. 20, 2019

(65) Prior Publication Data
US 2020/0155132 A1 May 21, 2020

Related U.S. Application Data

(63) Continuation of application No. PCT/US2018/023800, filed on Mar. 22, 2018.
(Continued)

(51) Int. Cl.
*A61B 17/00* (2006.01)
*A61B 17/34* (2006.01)
(Continued)

(52) U.S. Cl.
CPC .... *A61B 17/00234* (2013.01); *A61B 17/3478* (2013.01); *A61B 2017/0084* (2013.01);
(Continued)

(58) Field of Classification Search
CPC .......... A61B 17/00234; A61B 17/3478; A61B 2017/00247; A61B 2017/00323;
(Continued)

(56) References Cited

U.S. PATENT DOCUMENTS

| | | | |
|---|---|---|---|
| 5,370,675 | A | 12/1994 | Edwards et al. |
| 5,520,685 | A | 5/1996 | Wojciechowicz |

(Continued)

FOREIGN PATENT DOCUMENTS

| | | |
|---|---|---|
| WO | WO 2005/063321 | 7/2005 |
| WO | WO 2009/061848 | 5/2009 |

(Continued)

OTHER PUBLICATIONS

Extended European Search Report for European Application No. 18771884.6, dated Nov. 23, 2020, 7 pages.
(Continued)

*Primary Examiner* — Ashley L Fishback

(57) ABSTRACT

The present invention provides transseptal puncture devices configured to access structures on the left side of the heart from the right side of the heart without requiring open-heart surgery. The devices have adjustable stiffness to enter the vasculature in a flexible, atraumatic fashion, then become rigid once in place to provide a stable platform for penetration of the fossa ovalis. The devices are further configured to controllably and stably extend a needle to puncture the FO. The devices include an indwelling blunt stylus that can extend perpendicularly from the device to increase the accuracy of placement near the fossa ovalis.

30 Claims, 18 Drawing Sheets

Related U.S. Application Data

(60) Provisional application No. 62/580,165, filed on Nov. 1, 2017, provisional application No. 62/474,939, filed on Mar. 22, 2017.

(51) Int. Cl.
  *A61B 17/3207*   (2006.01)
  *A61M 25/01*   (2006.01)
  *A61B 18/00*   (2006.01)

(52) U.S. Cl.
  CPC .............. *A61B 2017/00247* (2013.01); *A61B 2017/00314* (2013.01); *A61B 2017/00323* (2013.01); *A61B 2017/320791* (2013.01); *A61B 2017/3405* (2013.01); *A61B 2017/3413* (2013.01); *A61B 2017/3454* (2013.01); *A61B 2017/3486* (2013.01); *A61B 2018/00392* (2013.01); *A61M 25/0108* (2013.01)

(58) Field of Classification Search
  CPC .... A61B 2017/3405; A61B 2017/3413; A61B 2017/3454; A61B 2017/3486; A61M 25/0108
  See application file for complete search history.

(56) References Cited

U.S. PATENT DOCUMENTS

| | | |
|---|---|---|
| 6,314,962 B1 | 11/2001 | Vaska et al. |
| 6,645,225 B1 | 11/2003 | Atkinson |
| 6,650,923 B1 * | 11/2003 | Lesh ................. A61B 17/3478 600/407 |
| 7,112,197 B2 | 9/2006 | Hartley et al. |
| 7,553,625 B2 | 6/2009 | Hoon et al. |
| 7,635,353 B2 | 12/2009 | Gurusamy et al. |
| 7,976,551 B1 | 7/2011 | Gutfinger et al. |
| 7,993,909 B2 | 8/2011 | Hoon et al. |
| 8,000,809 B2 | 8/2011 | Elencwajg |
| 8,019,404 B2 | 9/2011 | Kapadia |
| 8,029,470 B2 | 10/2011 | Whiting et al. |
| 8,084,246 B2 | 12/2011 | Hoon et al. |
| 8,114,110 B2 | 2/2012 | Bednarek et al. |
| 8,235,916 B2 | 8/2012 | Whiting et al. |
| 8,317,810 B2 | 11/2012 | Stangenes et al. |
| 8,333,687 B2 | 12/2012 | Farnan et al. |
| 8,343,029 B2 | 1/2013 | Farnan et al. |
| 8,388,549 B2 | 3/2013 | Paul et al. |
| 8,394,010 B2 | 3/2013 | Farnan |
| 8,460,168 B2 | 6/2013 | Farnan |
| 8,491,619 B2 | 7/2013 | Breznock |
| 8,694,077 B2 | 4/2014 | Kapadia |
| 8,784,291 B2 | 7/2014 | Farnan et al. |
| 8,821,366 B2 | 9/2014 | Farnan et al. |
| 8,831,707 B2 | 9/2014 | Tekulve et al. |
| 8,900,193 B2 | 12/2014 | Paul et al. |
| 8,940,008 B2 | 1/2015 | Kunis |
| 8,961,550 B2 | 2/2015 | Lenker et al. |
| 8,979,750 B2 | 3/2015 | Van Bladel et al. |
| 8,986,264 B2 | 3/2015 | Kimmel et al. |
| 8,996,135 B2 | 3/2015 | Elencwajg |
| 9,022,916 B2 | 5/2015 | Farnan et al. |
| 9,028,393 B2 | 5/2015 | Farnan |
| 9,050,064 B2 | 6/2015 | Kassab et al. |
| 9,095,363 B2 | 8/2015 | Van Bladel et al. |
| 9,173,711 B2 | 11/2015 | Butler et al. |
| 9,173,712 B2 | 11/2015 | Annest et al. |
| 9,198,756 B2 | 12/2015 | Aklog et al. |
| 9,211,367 B2 | 12/2015 | Farnan et al. |
| 9,220,417 B2 | 12/2015 | Paul et al. |
| 9,289,577 B2 | 3/2016 | Gurley et al. |
| 9,301,759 B2 | 4/2016 | Spivey et al. |
| 9,314,595 B2 | 4/2016 | Gurley |
| 9,320,513 B2 | 4/2016 | Van Bladel et al. |
| 9,326,756 B2 | 5/2016 | Stangenes et al. |
| 9,358,039 B2 | 6/2016 | Kimmel et al. |
| 9,415,148 B2 | 8/2016 | Farnan |
| 9,445,836 B2 | 9/2016 | Breznock |
| 9,486,206 B2 | 11/2016 | Annest et al. |
| 9,492,623 B2 | 11/2016 | Kapadia et al. |
| 9,498,584 B2 | 11/2016 | Kapadia et al. |
| 9,498,585 B2 | 11/2016 | Kapadia et al. |
| 9,545,265 B2 | 1/2017 | Maisano et al. |
| 9,597,146 B2 | 3/2017 | Davies et al. |
| 9,662,212 B2 | 5/2017 | Van Bladel et al. |
| 9,700,351 B2 | 7/2017 | Maisano et al. |
| 9,707,007 B2 | 7/2017 | Lenker et al. |
| 9,788,858 B2 | 10/2017 | Maisano et al. |
| 9,855,021 B2 | 1/2018 | Abraham |
| 9,937,043 B2 | 4/2018 | Van Bladel et al. |
| 9,962,184 B2 | 5/2018 | Paul et al. |
| 10,004,879 B2 | 6/2018 | Gurley |
| 10,016,210 B2 | 7/2018 | Lenker et al. |
| 10,034,686 B2 | 7/2018 | Breznock |
| 10,092,726 B2 | 10/2018 | Gurley et al. |
| 10,179,049 B2 | 1/2019 | Van Bladel et al. |
| 10,208,290 B2 | 2/2019 | Zhu et al. |
| 10,219,904 B2 | 3/2019 | Butler et al. |
| 10,220,134 B2 | 3/2019 | Kunis |
| 10,307,569 B2 | 6/2019 | Kunis |
| 10,314,641 B2 | 6/2019 | Paul et al. |
| 10,398,503 B2 | 9/2019 | Sapir et al. |
| 10,485,569 B2 | 11/2019 | Lenker et al. |
| 10,500,371 B2 | 12/2019 | Sapir et al. |
| 11,045,224 B2 | 6/2021 | Gammie et al. |
| 11,154,325 B2 | 10/2021 | Gammie et al. |
| 11,172,960 B2 | 11/2021 | Gammie et al. |
| 2004/0092973 A1 | 5/2004 | Chanduszko et al. |
| 2005/0010203 A1 | 1/2005 | Edwards et al. |
| 2005/0119670 A1 | 6/2005 | Kerr |
| 2005/0153309 A1 | 7/2005 | Hoon et al. |
| 2006/0020276 A1 | 1/2006 | Saadat et al. |
| 2006/0079769 A1 | 4/2006 | Whiting et al. |
| 2006/0079787 A1 | 4/2006 | Whiting et al. |
| 2006/0196137 A1 | 9/2006 | Brenzel et al. |
| 2007/0021767 A1 | 1/2007 | Breznock |
| 2007/0043318 A1 | 2/2007 | Sogard et al. |
| 2007/0083168 A1 | 4/2007 | Whiting et al. |
| 2007/0173757 A1 | 7/2007 | Levine et al. |
| 2007/0270751 A1 | 11/2007 | Stangenes et al. |
| 2009/0105742 A1 | 4/2009 | Kurth et al. |
| 2010/0114184 A1 | 5/2010 | Degtyar et al. |
| 2011/0022057 A1 | 1/2011 | Eigler et al. |
| 2011/0087261 A1 | 4/2011 | Wittkampf et al. |
| 2011/0238102 A1 | 9/2011 | Gutfinger et al. |
| 2011/0245800 A1 | 10/2011 | Kassab et al. |
| 2012/0041422 A1 | 2/2012 | Whiting et al. |
| 2012/0078061 A1 | 3/2012 | Calafiore et al. |
| 2013/0085388 A1 | 4/2013 | Stangenes et al. |
| 2013/0304036 A1 | 11/2013 | Kimmel et al. |
| 2013/0304051 A1 | 11/2013 | Kimmel et al. |
| 2014/0148828 A1 | 5/2014 | Ewers et al. |
| 2014/0171870 A1 | 6/2014 | Kapadia |
| 2014/0206961 A1 | 7/2014 | Hoon et al. |
| 2014/0236205 A1 | 8/2014 | Jabba et al. |
| 2014/0309679 A1 | 10/2014 | Maisano et al. |
| 2015/0165159 A1 | 6/2015 | Elencwajg |
| 2015/0238729 A1 | 8/2015 | Jenson et al. |
| 2015/0258270 A1 | 9/2015 | Kunis |
| 2015/0265344 A1 | 9/2015 | Aktas et al. |
| 2016/0007896 A1 | 1/2016 | Hoon et al. |
| 2016/0058489 A1 | 3/2016 | Fischell et al. |
| 2016/0095600 A1 | 4/2016 | Annest et al. |
| 2016/0100859 A1 | 4/2016 | Sapir et al. |
| 2016/0193449 A1 | 7/2016 | Sarabia et al. |
| 2016/0270837 A1 | 9/2016 | Cheng et al. |
| 2017/0001000 A1 | 1/2017 | Beach |
| 2017/0014113 A1 | 1/2017 | Ma |
| 2017/0105761 A1 | 4/2017 | Sapir et al. |
| 2017/0303961 A1 | 10/2017 | Sapir et al. |
| 2018/0000516 A1 | 1/2018 | Maisano et al. |
| 2018/0263658 A1 | 9/2018 | Drasler |
| 2018/0289388 A1 | 10/2018 | Lenker et al. |
| 2018/0317949 A1 | 11/2018 | Lenker et al. |

(56) References Cited

U.S. PATENT DOCUMENTS

| | | |
|---|---|---|
| 2018/0333170 A1 | 11/2018 | Breznock |
| 2019/0029750 A1 | 1/2019 | Maini |
| 2019/0046236 A1 | 2/2019 | Kassab et al. |
| 2019/0209808 A1 | 7/2019 | Gurley et al. |
| 2019/0274833 A1 | 9/2019 | Van Bladel et al. |
| 2019/0298411 A1 | 10/2019 | Davies et al. |
| 2019/0336163 A1 | 11/2019 | McNamara et al. |
| 2020/0229805 A1 | 7/2020 | Gammie et al. |
| 2020/0246046 A1 | 8/2020 | Gammie et al. |
| 2021/0196320 A1 | 7/2021 | Gammie et al. |
| 2021/0259738 A1 | 8/2021 | Gammie et al. |

FOREIGN PATENT DOCUMENTS

| | | |
|---|---|---|
| WO | WO 2016/009337 | 1/2016 |
| WO | WO 2017/139463 | 8/2017 |
| WO | WO 2018/175743 | 9/2018 |
| WO | WO-2020068841 A1 | 4/2020 |
| WO | WO-2021195243 | 9/2021 |

OTHER PUBLICATIONS

Office Action for U.S. Appl. No. 16/787,747, dated May 26, 2020, 23 pages.

Office Action for U.S. Appl. No. 16/787,747, dated Dec. 1, 2020, 24 pages.

Office Action for U.S. Appl. No. 16/858,015, dated Sep. 23, 2020, 17 pages.

Office Action for U.S. Appl. No. 16/858,015, dated Feb. 4, 2021, 18 pages.

Invitation to Pay Additional Fees and Partial International Search Report for International Application No. PCT/US2019/052714, dated Dec. 5, 2019, 14 pages.

International Search Report and Written Opinion for International Application No. PCT/US2019/052714, dated Jan. 29, 2020, 19 pages.

International Search Report and Written Opinion for International Application No. PCT/US2018/023800, dated Jun. 1, 2018, 12 pages.

International Search Report and Written Opinion for International Application No. PCT/US2021/023930, dated Jul. 1, 2021, 7 pages.

International Search Report and Written Opinion for International Application No. PCT/US2022/011623, dated Apr. 1, 2022, 10 pages.

Notice of Reasons for Rejection for Japanese Application No. 2020-501425, dated May 26, 2022, 9 pages.

Office Action for European Application No. 19783853.5, dated May 25, 2022, 6 pages.

Office Action for U.S. Appl. No. 17/315,729, dated Jul. 20, 2021, 16 pages.

Office Action for U.S. Appl. No. 17/192,329, dated Jun. 3, 2021, 18 pages.

\* cited by examiner

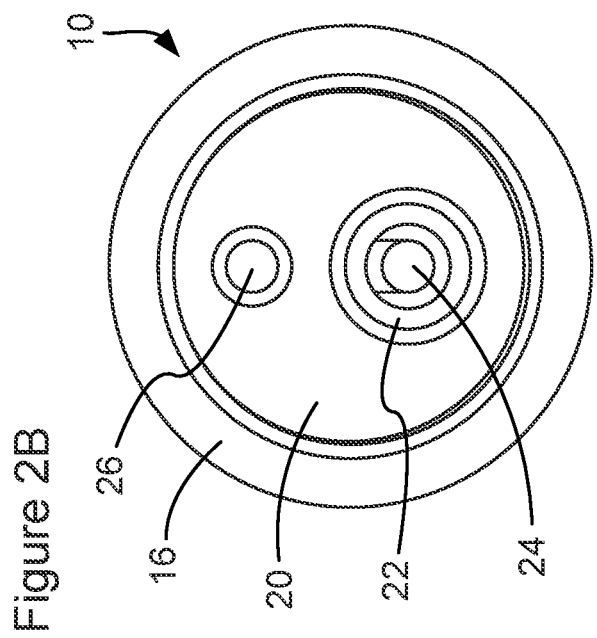
Figure 2B
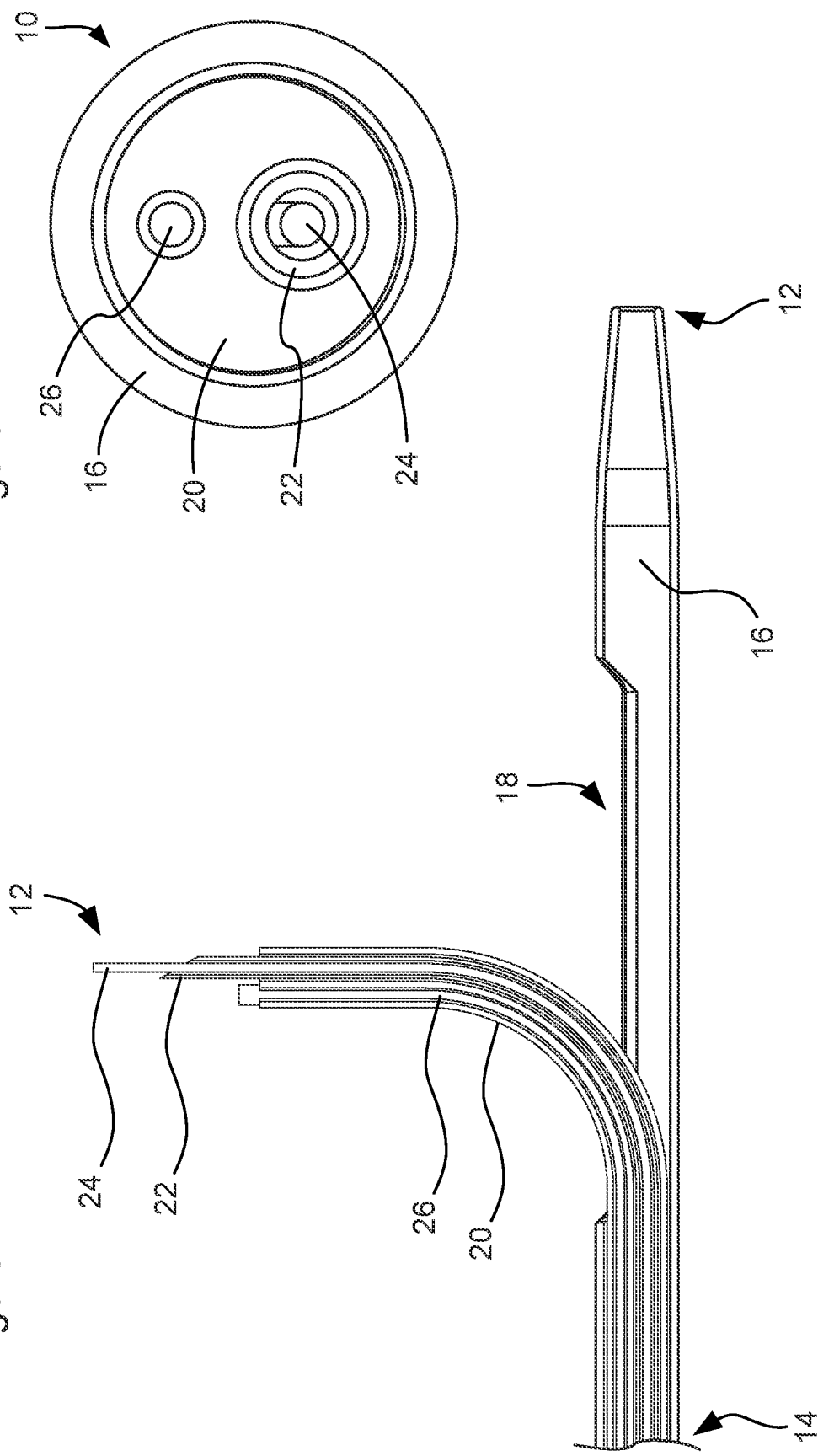
Figure 2A
Figure 2A - Figure 2B

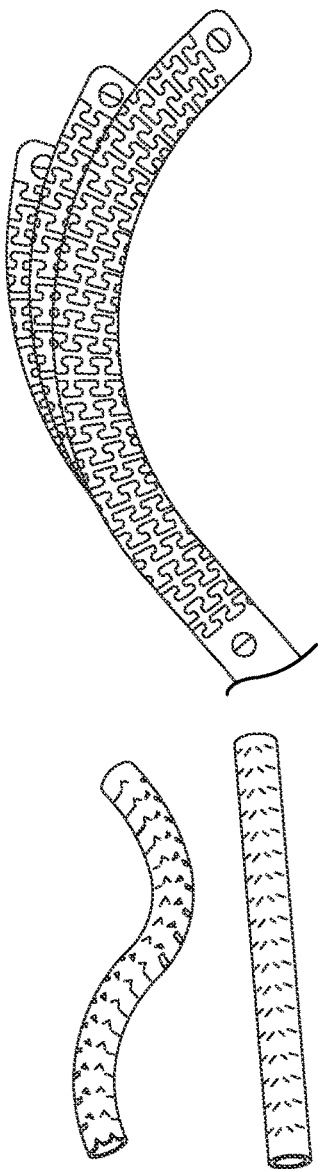
Figure 2C
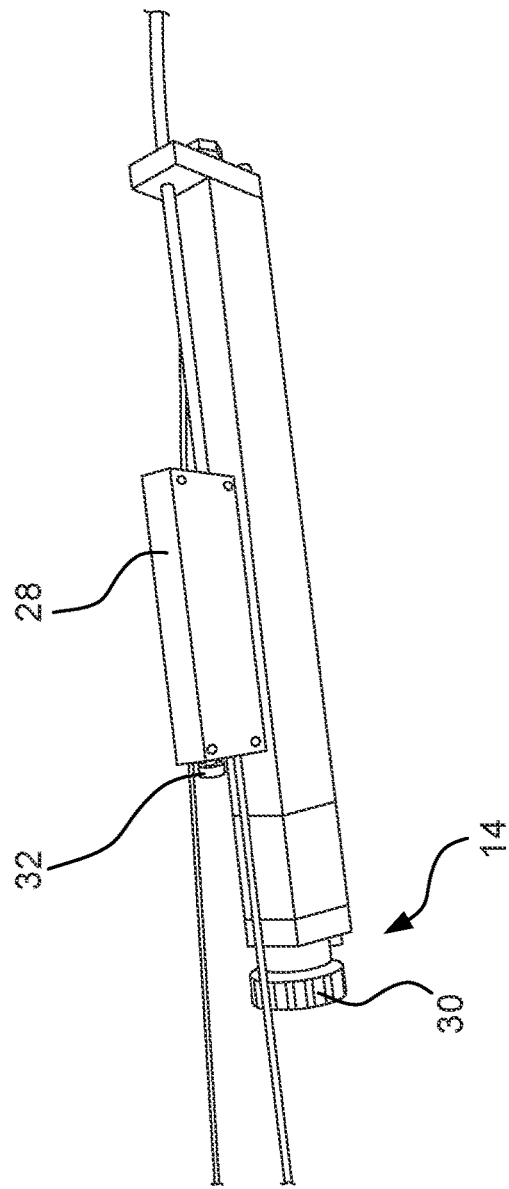
Figure 2D
Figure 2C - Figure 2D

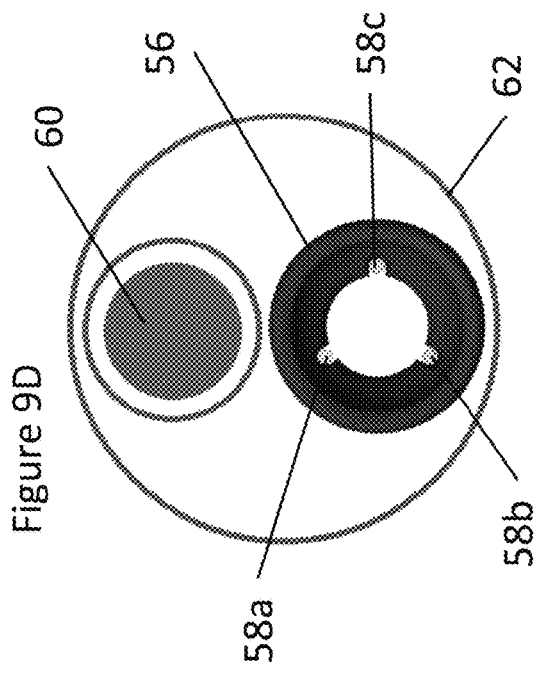
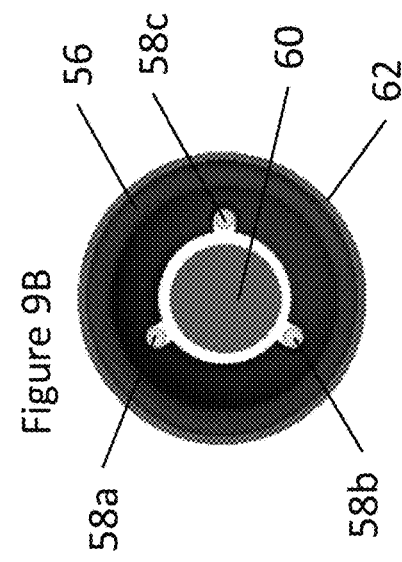
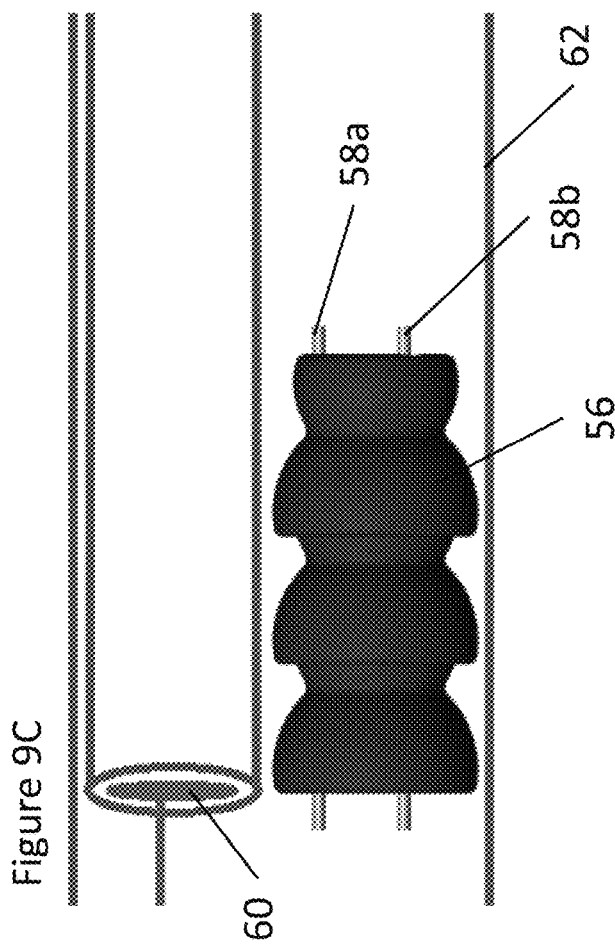
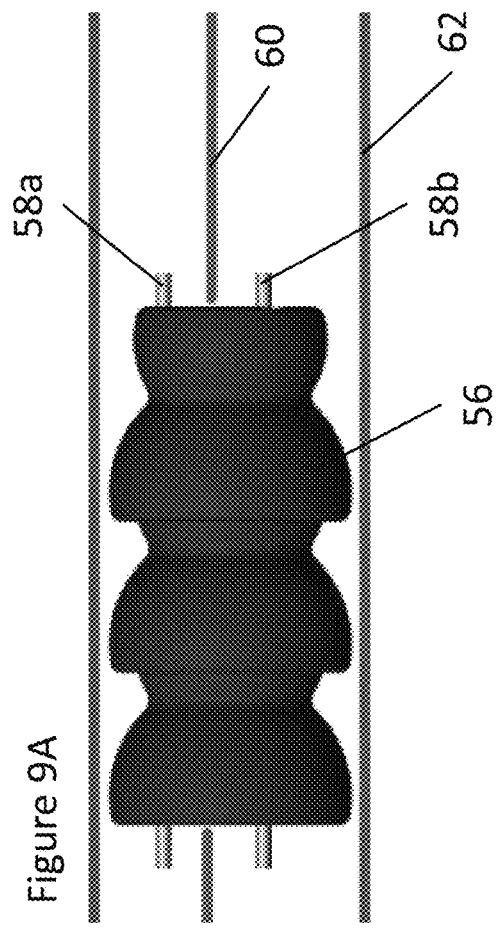

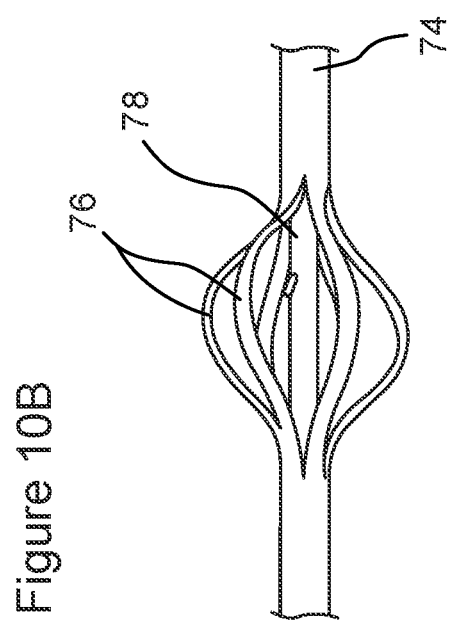
Figure 10A
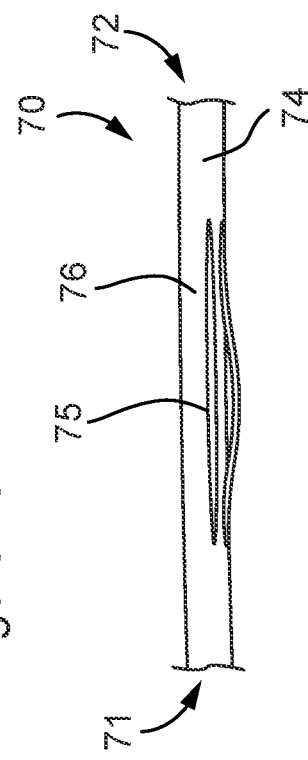
Figure 10B
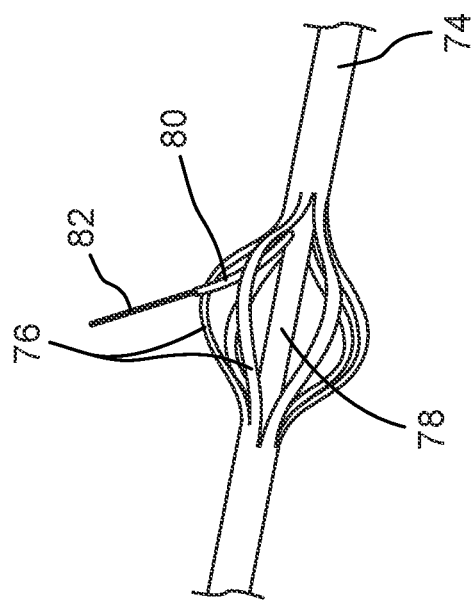
Figure 10C
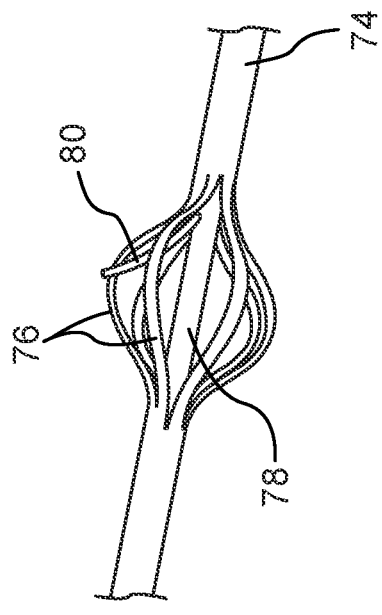
Figure 10D
Figure 10A - Figure 10D

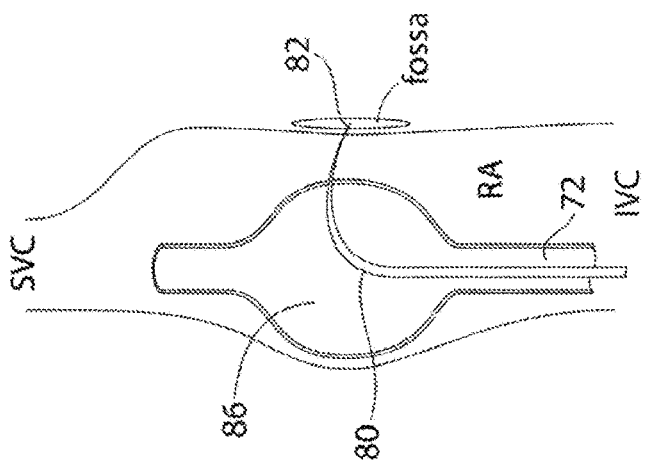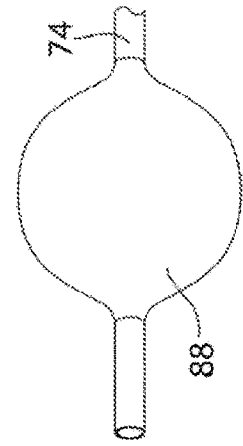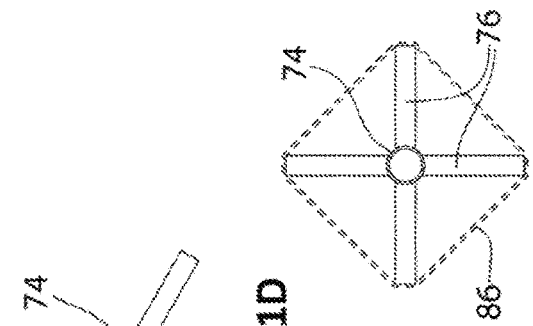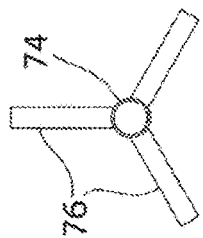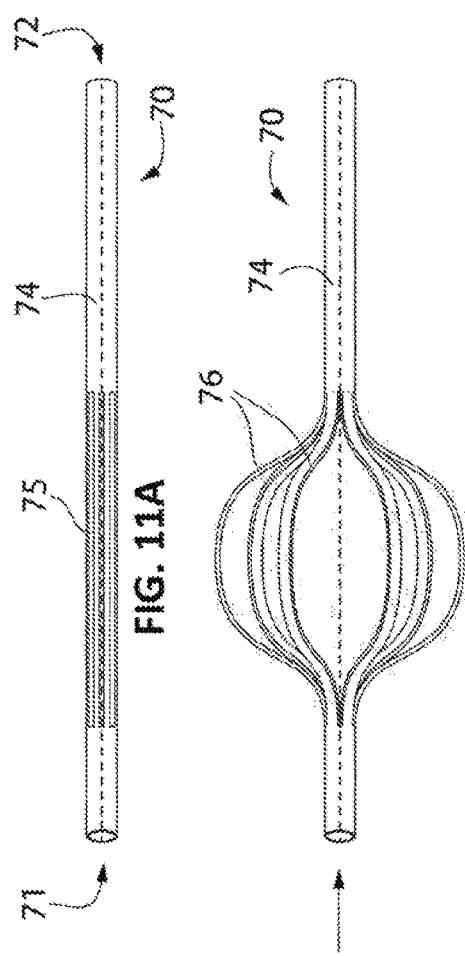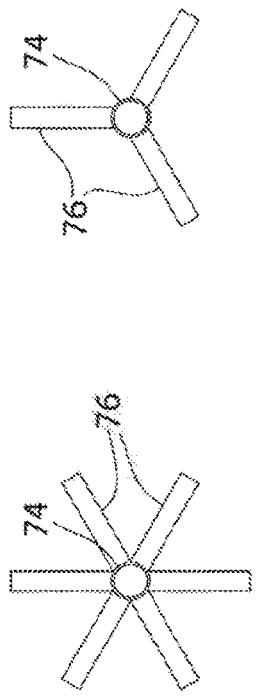

Figure 12A
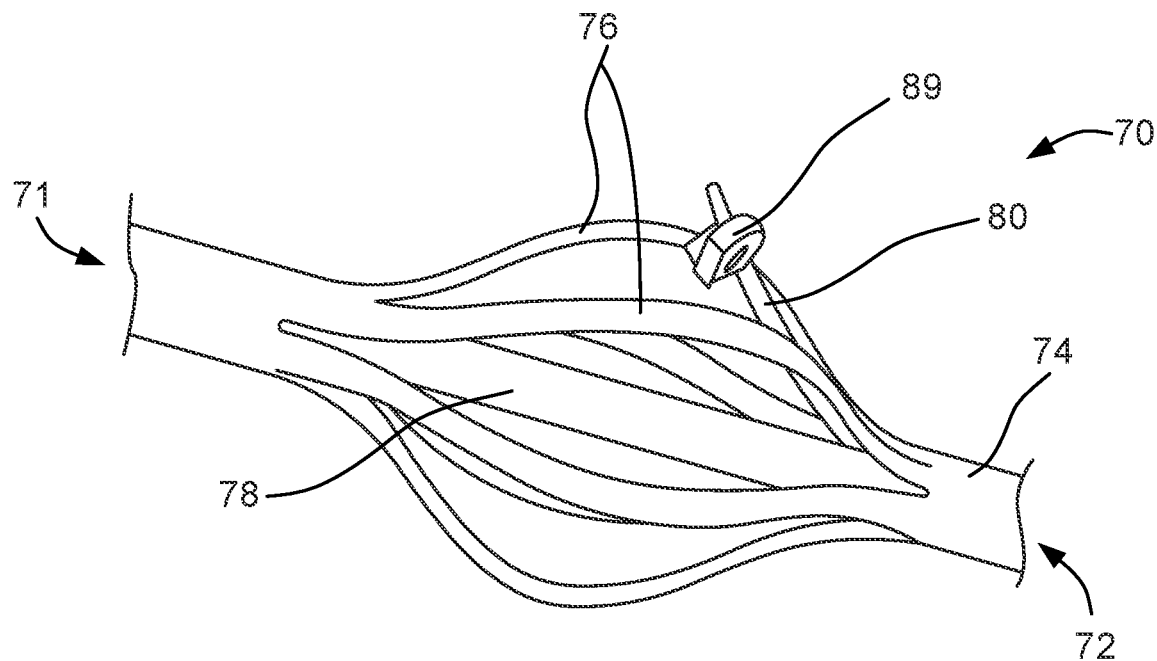
Figure 12B
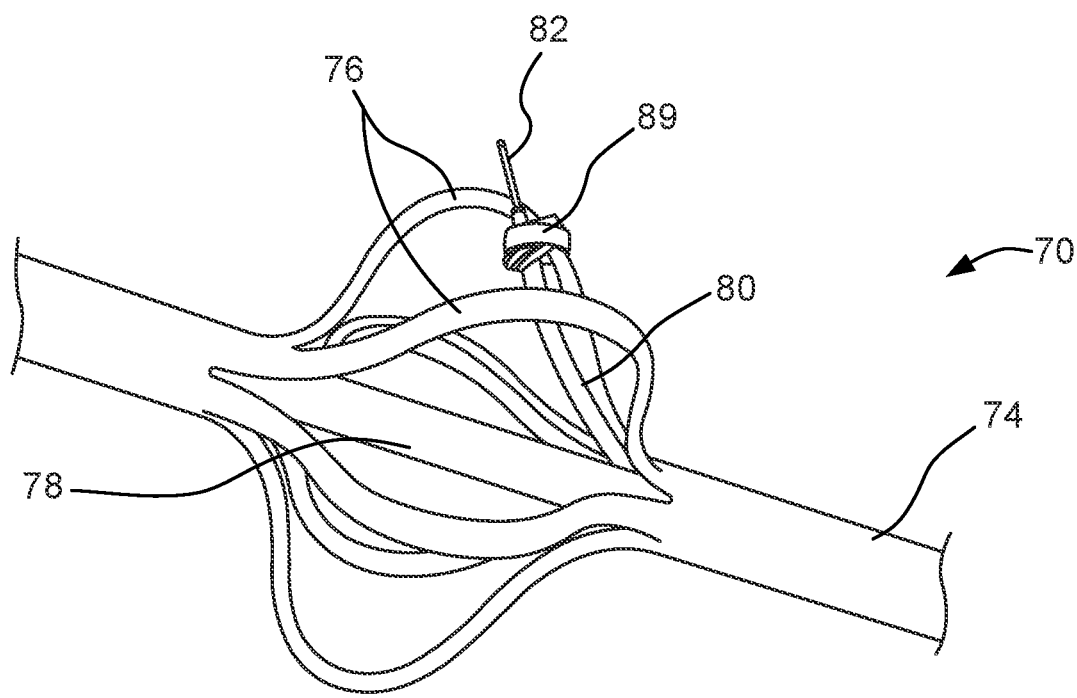
Figure 12A - Figure 12B

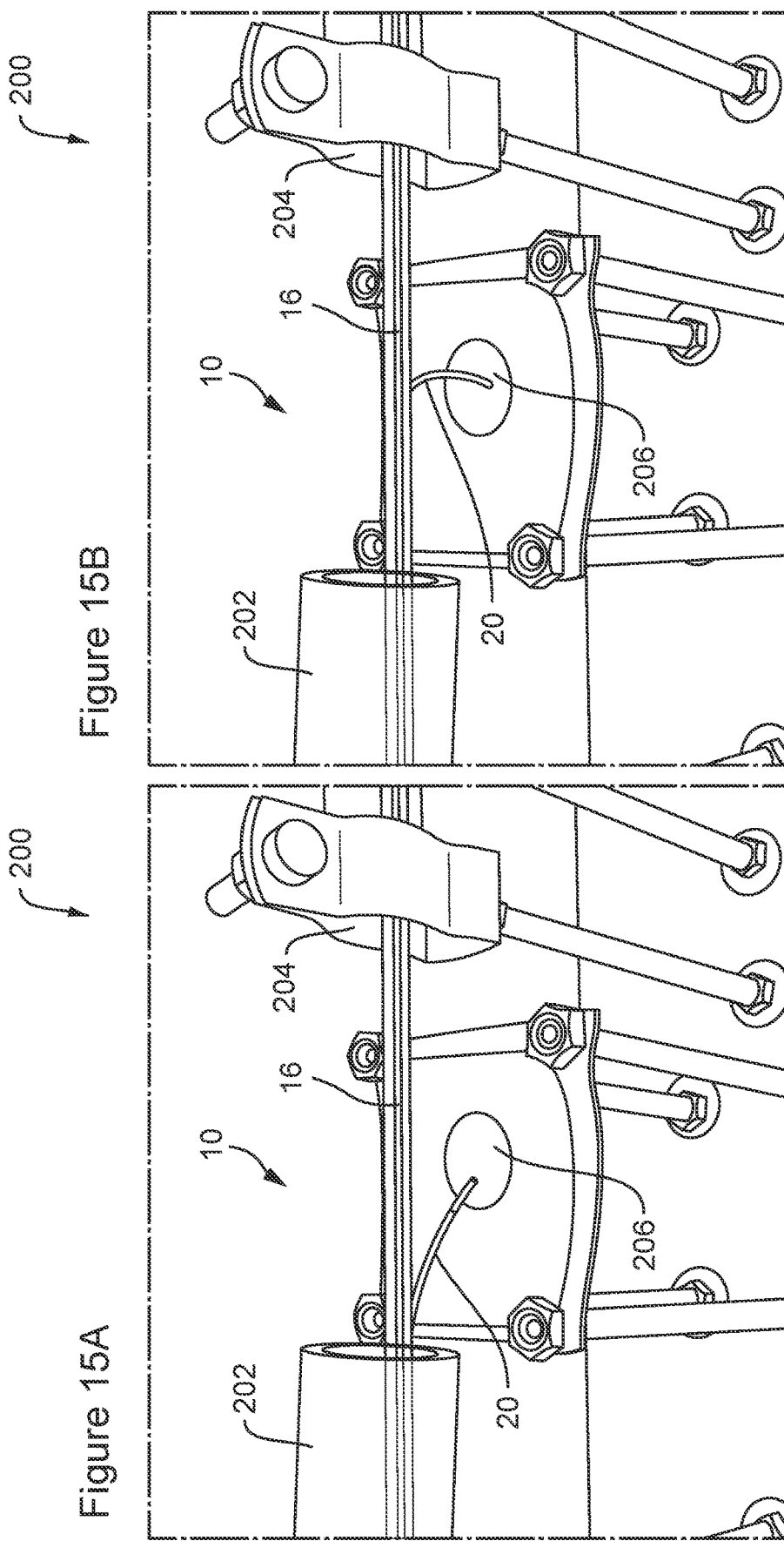
Figure 15A — Figure 15B

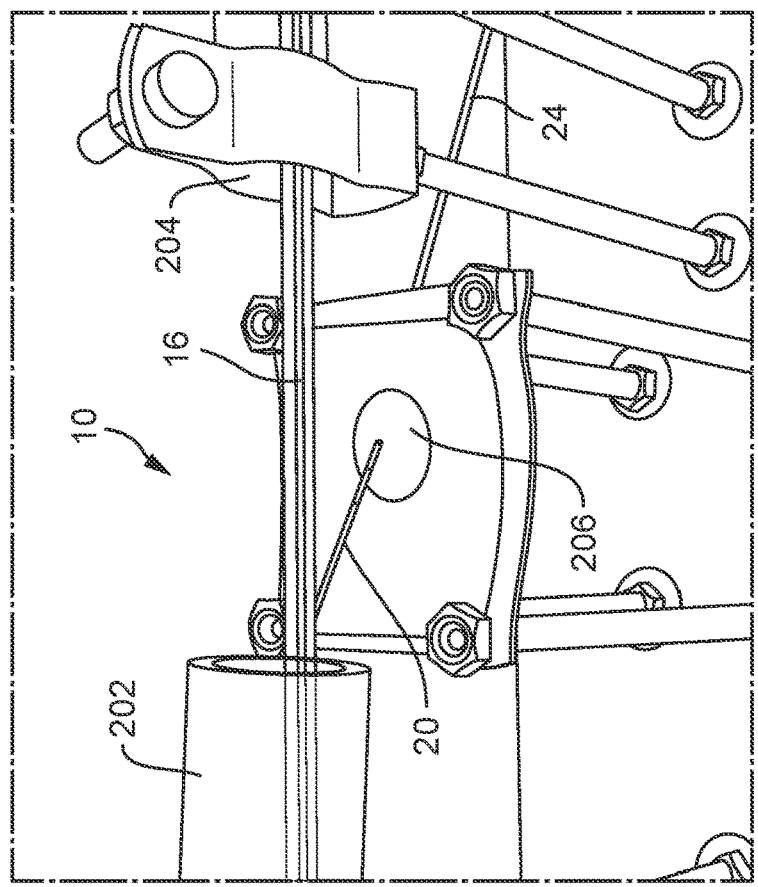
Figure 15C
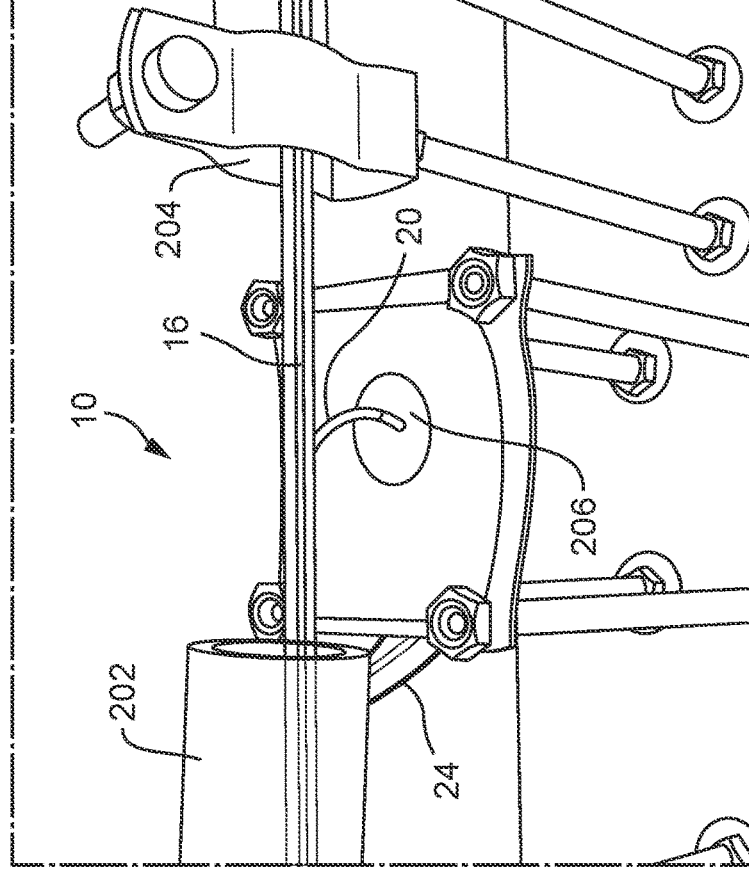
Figure 15D
Figure 15C - Figure 15D

DEVICE AND METHOD FOR TRANSSEPTAL PUNCTURE

CROSS-REFERENCE TO RELATED APPLICATIONS

This application is a continuation of International Patent Application No. PCT/US2018/023800, filed Mar. 22, 2018, entitled Device and Method for Transseptal Puncture," which claims priority to U.S. Provisional Patent Application No. 62/474,939, filed Mar. 22, 2017, and to U.S. Provisional Patent Application No. 62/580,165, filed Nov. 1, 2017, the contents of each of which are incorporated by reference herein in their entirety.

BACKGROUND OF THE INVENTION

Atrial fibrillation (AF) and mitral valve (MV) disease are two common disorders impacting the left side of the heart. In AF, disordered rhythmic contractions of the upper chambers of the heart can lead to blood clot formation and stroke. AF impacts between 2.7 and 6.1 million American adults and is projected to impact almost 15.9 million people by 2050. The lifetime risk of AF development in Caucasian men over 40 years of age is 26%, with AF contributing to greater than 99,000 deaths per year. Patients with AF have more frequent hospitalizations, a 5-fold greater risk of stroke, twice the risk of dementia, and twice the mortality rate than those patients without AF. A diagnosis of AF adds $8,700/year to the individual cost of treatment with an estimated impact of $26 billion/year on healthcare in the United States. For the treatment of AF, the use of catheter-based ablation technology is increasing at a rate of approximately 15% per year, and in the U.S., almost $30 billion is spent each year on cardiac rhythm management devices and ablation procedures.

MV disease is the most common cardiac lesion, impacting 1.7% of the U.S. adult population (9.3% of individuals ≥75 years of age), with an estimated cost per hospitalization of $51,415. Symptomatic MV heart disease increases annual health care expenditures by $7.6 billion in the U.S., with an overall total incremental expenditure for valvular heart disease of $23.4 billion. The treatment of mitral regurgitation in high risk populations by a catheter-based device (MitraClip, Abbot Vascular) has been used in over 25,000 patients and Edwards LifeSciences estimates that transcatheter valve products will account for almost a quarter of 2017 revenue ($2,373.1 million).

The surge in available catheter-based cardiovascular devices represents an area of enormous potential with regards to the development of technology to enhance and improve device delivery. Access to the left side of the heart is challenging and not without risk. Current catheter-based procedures rely on dated technology as the platform for device delivery, which often begin via transseptal puncture (TSP), in which a catheter containing a sheathed needle is advanced from the femoral vein in the groin to the superior vena cava (SVC) through the right atrium (RA) of the heart. The catheter assembly is gently pulled out of the SVC and into the RA until the tip rests within the fossa ovalis (FO), a small, thin membrane separating the RA from the left atrium (LA). The location of the FO is determined by ultrasound and fluoroscopy, under which the catheter assembly is observed to make two 'jumps' as it is pulled back from the SVC and into the RA (jump one), subsequently landing in the FO (jump two). The catheter assembly is pushed against the FO, visibly 'tenting' the delicate tissue, after which the needle is deployed and the FO penetrated. Once the catheter enters the LA, the needle is removed and a desired device (e.g., AF ablation device) can be inserted and used. While simple in theory, several components of the procedure present special challenges that can be addressed by novel technology.

The typical catheter (Mullins TS introducer, Medtronic, Minneapolis, Minn.) and needle (Brockenbrough, Medtronic) assembly is little altered from the first system created in the 1960s by Ross, Braunwald, and Morrow (FIG. 1). The catheter has a curve on the end. The catheter is extremely flexible and not very stable within the SVC and is easily maneuvered out of position, especially during normal dynamic cardiac activity. While tightly fitting, the catheter and needle assembly are not interlocking. If the position of the needle/assembly is not purposefully maintained, accidental needle exposure can occur. Further complicating this procedure is potentially distorted anatomy due to aortic or MV disease, leading to changes in the location of the FO and obfuscation of typical anatomical landmarks. In patients undergoing a repeat procedure, the FO may be thickened and scarred, necessitating application of greater puncturing force and increasing the likelihood of damage to unintended structures (Katritsis G D et al., International journal of cardiology, 2013, 168(6):5352-5354.). Additionally, as the needle is relatively stiff with a permanent bend at the distal end, forcible straightening of the needle as it passes through the dilator may result in the needle scraping plastic shavings from the inside of the dilator (Han S-W et al., International Journal of Arrhythmia, 2010, 11(4):4-17; Hsu J C et al., Journal of the American Heart Association, 2013, 2(5): e000428).

Unintended or misaligned FO puncture can lead to inadvertent perforation of the aortic root, coronary sinus, or posterior free wall of the RA, all of which are potentially fatal (Katritsis G D et al., International journal of cardiology, 2013, 168(6):5352-5354.). The failure rate of transseptal procedures can be as high as 8%, with instrument-related causes contributing to almost 10% of failed punctures. The increase in medical costs to patients undergoing a repeat procedure is approximately 46% and a reduction in the rate of repeat procedures by only 1% could save the U.S. healthcare system almost $30 million. There is a steep learning curve associated with transseptal procedures (at least 29 procedures are required to attain proficiency), with the majority of improper punctures occurring in individuals with the least amount of experience (Katritsis G D et al., International journal of cardiology, 2013, 168(6):5352-5354.), and greater procedure success rates seen in higher volume centers. In the past, the majority of TSPs were performed by physicians in an electrophysiology lab. Recently, more and more cardiologists and cardiac surgeons are performing these procedures, and as such, are demanding more intuitive devices that can be operated in a shorter period of time. Indeed, the amount of time needed to perform TSP is a significant limiting factor to current catheter-based interventions. Eleid et al. in describing their first 75 MitraClip procedures, found that the time from procedure start to TSP averaged 40 minutes, with no noticeable decrease in procedure time over the course of the 75 cases (r=0.03) (Eleid M F et al., JACC Cardiovascular interventions, 2015, 8(7):e117-9.).

Therefore, there is a need in the art for improved transseptal access devices providing increased stability, adequate visualization of the fossa ovalis, and accurate and timely deployment. The present invention addresses this need.

SUMMARY OF THE INVENTION

In one aspect, the present invention provides a transseptal puncture device comprising: an elongate tubular member having a hollow interior, a distal end, a proximal end, and at least one window to the hollow interior positioned near the distal end; an elongate stylus positioned within the hollow interior of the tubular member, the stylus having a distal end, a proximal end, and a lumen throughout; and a handle positioned at the proximal end of the tubular member, the handle mechanically linked to the stylus and configured to bend the distal end of the stylus out of the at least one window of the tubular member.

In one embodiment, the mechanical link between the handle and the stylus comprises at least one pull cable attached to the distal end of the stylus. In one embodiment, the mechanical link between the handle and the stylus is further configured to advance and retract the stylus within the tubular member. In one embodiment, the mechanical link between the handle and the stylus is further configured to stiffen and relax the stylus.

In one embodiment, the lumen of the stylus is sized to fit a hollow needle having a guidewire, the needle and guidewire being mechanically linked to the handle. In one embodiment, the tubular member has a diameter between about 5 mm and 7 mm. In one embodiment, the tubular member has a lubricant coating, an anticoagulant coating, or both. In one embodiment, the stylet has an articulated section at its distal end. In one embodiment, the length of the articulated section is between about 2 cm and 4 cm. In one embodiment, the distal end of the stylus bends at an angle of between about 0 degrees and 90 degrees away from the tubular member. In one embodiment, the device further comprises at least one radiopaque or echo-bright marker positioned at the distal end of the tubular member, the stylus, or both.

In one embodiment, the lumen of the stylus is sized to fit an elongate tubular, flat-end-effector-tipped member, the flat-end-effector-tipped member having a lumen running throughout sized to fit a hollow needle having a guidewire. In one embodiment, the flat-end-effector-tipped member comprises an undulated bell-shaped tip having an open diameter of between about 8 mm and 15 mm and a collapsible diameter of between about 5 mm and 7 mm. In one embodiment, the flat-end-effector-tipped member is configured to collapse by withdrawing into a sheath positioned at the distal end of the bendable member.

In one embodiment, the tubular member comprises a lumen having a loose spine and a pull cable. In one embodiment, the pull cable is configured to stiffen the spine when pulled.

In another aspect, the present invention provides a transseptal puncture device comprising: an elongate tubular member having at least one lumen running between a distal end and a proximal end; a plurality of interlocking hollow segments, each segment configured to connect to an adjacent segment by a ball joint to form an elongate hollow articulated member; at least three pull cables running through the articulated member attached to the distal-most segment, the pull cables being arranged equidistantly from each other in a radial pattern; and a handle positioned at the proximal end of the tubular member, the handle comprising at least three knobs configured to pull and release each of the at least three pull cables; wherein the at least three pull cables, when pulled, are configured to bend the distal end of the articulated member in the direction of the pulled cables.

In one embodiment, the hollow articulated member comprises a hollow needle having a guidewire. In one embodiment, the tubular member comprises a second lumen comprising a hollow needle having a guidewire.

In another aspect, the present invention provides a method of accessing the left atrium, comprising the steps of: providing a transseptal puncture device of the present invention; positioning the transseptal puncture device in a vena cava of a patient such that at least one window is adjacent to a fossa ovalis of the patient; extending a stylus through the at least one window of the transseptal puncture device to touch the fossa ovalis; advancing a needle through the stylus to pierce the fossa ovalis; advancing a guidewire through the needle past the fossa ovalis; retracting the needle and the stylus into the transseptal puncture device; and retracting the transseptal puncture device from the vena cava.

In one embodiment, a distal end of the transseptal puncture device is positioned above the superior vena cava. In one embodiment, the step of extending a stylus is preceded by a step of stiffening a cannula of the transseptal puncture device by compacting a spine in the cannula using a pull cable. In one embodiment, the step of advancing a needle is preceded by a step of extending a bell-tipped member to touch the fossa ovalis.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

FIG. 2A through FIG. 2D depict an exemplary transseptal puncture device of the present invention. FIG. 2A is a side cross-sectional view of the device. FIG. 2B is a frontal cross-sectional view of the device. FIG. 2C depicts exemplary stylus constructions of the device. FIG. 2D depicts an exemplary handle of the device.

FIG. 6A and FIG. 6B depict the atraumatic support stored within a sheath at the distal end of the device. FIG. 6C and FIG. 6D depict the atraumatic support deployed from the sheath.

FIG. 7A is a side cross-sectional view of the device. FIG. 7B is a frontal cross-sectional view of the device.

FIG. 8A depicts a distal portion of the device. FIG. 8B depicts a side view of a section of the device. FIG. 8C depicts a side cross-sectional view of a section of the device. FIG. 8D depicts a frontal cross-sectional view of the device.

FIG. 9A through FIG. 9D depict exemplary configurations of a segmented transseptal puncture device. FIG. 9A and FIG. 9B depict a side view and a frontal cross sectional view, respectively, of a section of a device having segmented sections positioned within a cannula and a needle positioned within the segmented sections. FIG. 9C and FIG. 9D depict a side view and a frontal cross sectional view, respectively, of a section of a device having segmented sections positioned within a cannula adjacent to a lumen containing a needle.

FIG. 10A through FIG. 10D depict an exemplary expanding transseptal puncture device. FIG. 10A depicts the device in an unexpanded configuration. FIG. 10B depicts the device in an expanded configuration. FIG. 10C depicts the device in an expanded configuration with a stylus extended through the sides of the device. FIG. 10D depicts the device in an expanded configuration with a needle extended through the extended stylus.

FIG. 11A through FIG. 11H depict further exemplary expanding transseptal puncture devices. FIG. 11A depicts the device in an unexpanded configuration. FIG. 11B depicts the device being expanded by retracting the end of the device. FIG. 11C depicts an exemplary device having six arms. FIG. 11D depicts an exemplary device having three arms. FIG. 11E depicts an exemplary device having a band secured around three arms. FIG. 11F depicts an exemplary device having a band secured around four arms. FIG. 11G depicts an exemplary device having a covering over a set of expanded arms (not visible). FIG. 11H depicts an exemplary device having a covering over a set of expanded arms secured in the right atrium of a patient, with an extended stylus penetrating through the covering and an extended needle penetrating through the fossa ovalis.

FIG. 12A and FIG. 12B depict a further exemplary expanding transseptal device. FIG. 12A depicts the device in an expanded configuration with a loop attached to one arm, the loop being secured to an extended stylus and securing the stylus to the one arm. FIG. 12B depicts the device with a needle being extended through the stylus secured to the extended arm by the loop.

FIG. 13A depicts the device with a hinged arm flush within a cannula. FIG. 13B depicts the device with the hinged arm rotating a stylus out of the cannula. FIG. 13C depicts a device having two hinged arms rotating a stylus out of a cannula.

FIG. 15A through FIG. 15E depict a series of images of an experimental setup investigating a prototype transseptal puncture device. FIG. 15A depicts the device positioned within an experimental inferior vena cava and an experimental superior vena cava with the stylus extending from the device towards an experimental fossa ovalis. FIG. 15B depicts the stylus extended fully against the experimental fossa ovalis, tenting the membrane. FIG. 15C depicts the insertion of a guidewire through the experimental fossa ovalis after successful puncture. FIG. 15D depicts the stylus partially retracted back into the device. FIG. 15E depicts the device fully withdrawn, leaving behind the guidewire traversing the experimental fossa ovalis.

DETAILED DESCRIPTION

Figure 1:
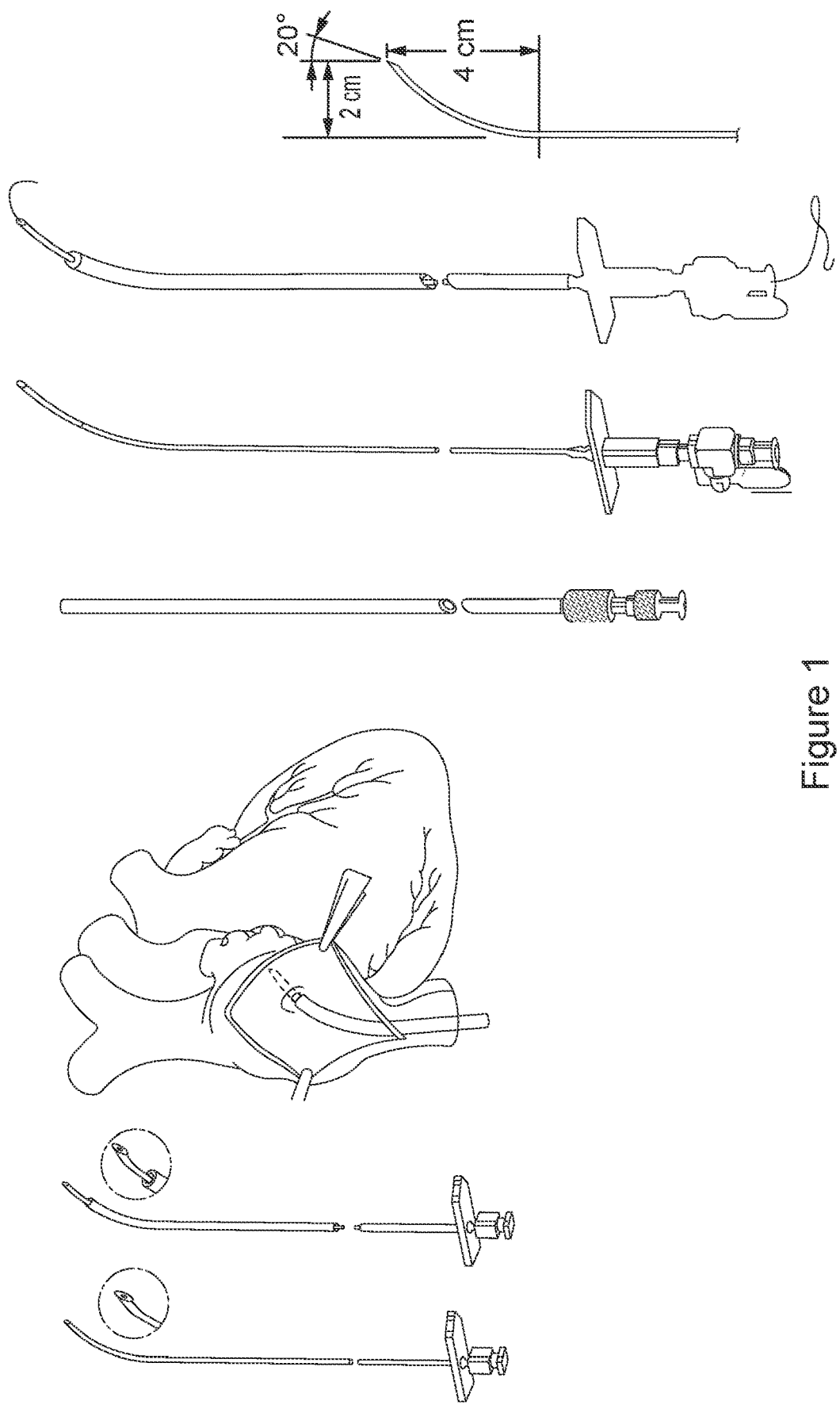
FIG. 1 depicts examples of typical transseptal puncture devices and a cross-sectional view of a heart illustrating the fossa ovalis (FO).

The present invention provides transseptal puncture devices configured to access structures on the left side of the heart from the right side of the heart without requiring open-heart surgery. The devices have adjustable stiffness to enter the vasculature in a flexible, atraumatic fashion, then become rigid once in place to provide a stable platform for penetration of the fossa ovalis. The devices are further configured to controllably and stably extend a needle to puncture the FO. The devices include an indwelling blunt stylus that can extend perpendicularly from the device to increase the accuracy of placement near the fossa ovalis.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments therebetween. This applies regardless of the breadth of the range.

Transseptal Puncture Device

The present invention provides devices that improve the targeting of the fossa ovalis during transseptal puncture and decrease the overall procedure time for transseptal puncture. The devices can be selectively stiffened to serve as a stable platform from which an arm extends in a controlled fashion to pierce the fossa ovalis. The devices increase the safety of transseptal puncture, reducing the likelihood that a minimally invasive procedure taking place in an electrophysiology lab needs to be moved to a surgical lab for open heart surgery. The devices are useful for interventional cardiologists, electrophysiologists, and cardiac surgeons to enhance minimally invasive or percutaneous procedures, including trans-catheter valve replacements, atrial fibrillation ablation, minimally invasive left ventricular assist devices, and the like.

Referring now to FIG. 2A through FIG. 2C, an exemplary transseptal puncture device 10 is depicted. Device 10 comprises a cannula 16 extending from a distal end 12 to a proximal end 14. Cannula 16 has an elongate hollow tubular shape having a lumen running throughout. Cannula 16 comprises an opening at its distal end 12 and at least one elongate window 18 adjacent to its distal end 12, wherein both the opening and the at least one window 18 are fluidly connected to the lumen of cannula 16. Cannula 16 can have any suitable dimensions. For example, cannula 16 can have an outer diameter of between about 14 and 22 French (about 5 mm to 7 mm). In some embodiments, cannula 16 can have one or more surface coatings. Suitable surface coatings can reduce friction or irritation, and can include anticoagulants such as heparin, EDTA, oxalate, and the like.

Device 10 further comprises an elongate, flexible, cylindrical stylus 20 sized to fit within the lumen of cannula 16. In certain embodiments, stylus 20 has an articulated construction, such as in FIG. 2C. The articulation can extend for the entire length of stylus 20, or only for a section of stylus 20. In some embodiments, stylus 20 is articulated for a length of between about 2 cm to 4 cm from distal end 12. Stylus 20 comprises a first lumen sized to fit a hollow needle 22. Hollow needle 22 also has a lumen running throughout, the lumen being sized to fit any suitable guidewire 24, such as a 0.035" guidewire. In various embodiments, stylus 20 comprises one or more additional lumen, each additional lumen sized to fit a cable 26.

Device 10 further comprises handle 28 at its proximal end 14. Handle 28 comprises an extension knob 30 and at least one angulation screw 32. Extension knob 30 is connected to the proximal end of stylus 20 and is actuatable to extend and retract stylus 20 within cannula 16. Each of the at least one angulation screw is connected to the proximal end of a cable 26 and is actuatable to extend and retract a connected cable 26 within stylus 20. In certain embodiments, handle 28 further comprises one or more actuatable knobs or screws connectable to needle 22 and guidewire 24, such that extension and retraction of needle 22 and guidewire 24 within stylus 20 may be achieved with precision.

Figure 3A:
FIG. 3A through FIG. 3D depict the range of deployment of an exemplary transseptal puncture device.
Figure 3B:
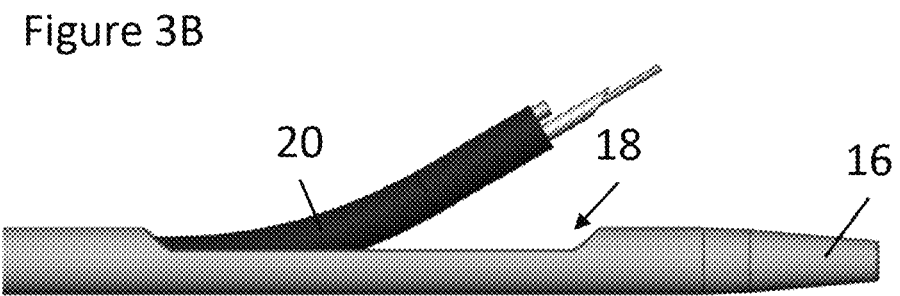
Figure 3C:
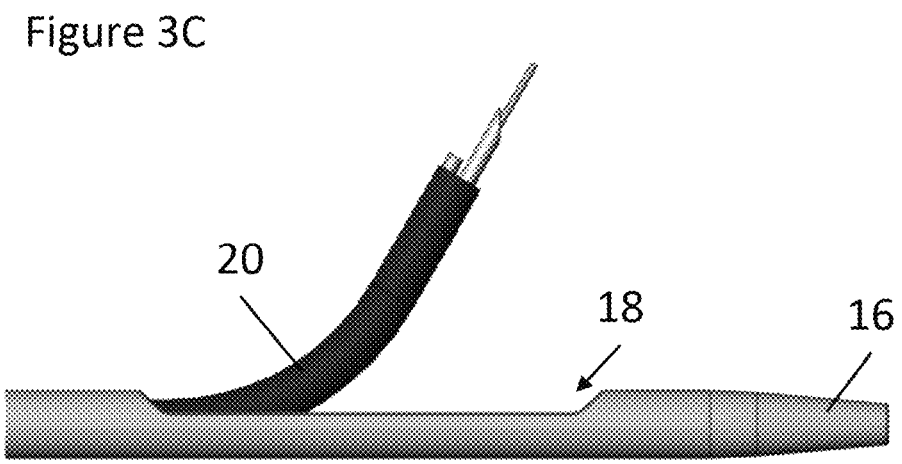
Figure 3D:
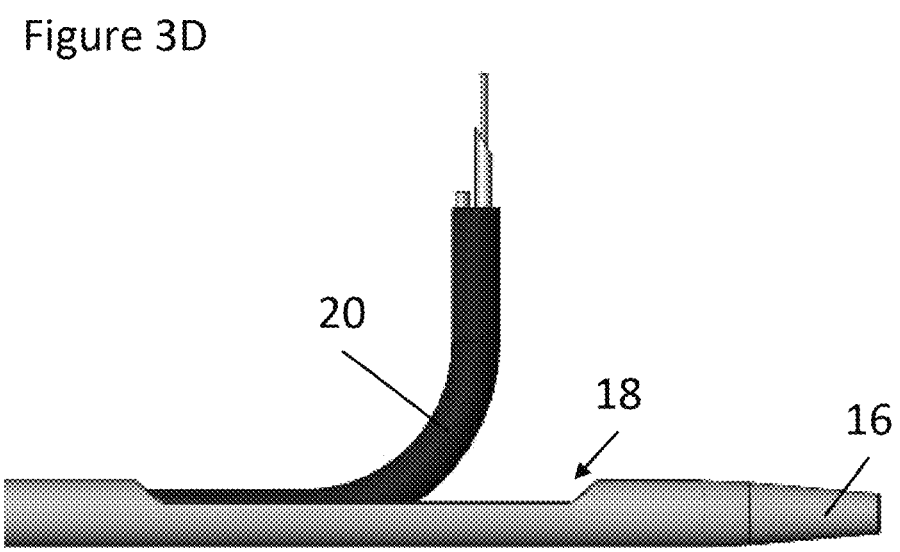

Referring now to FIG. 3A through FIG. 3D, device 10 is shown in several stages of stylus 20 deployment. In FIG. 3A, stylus 20 lies flush within cannula 16 and does not protrude out of window 18. In this configuration, cannula 16 may be manipulated to a desired location without being impeded by stylus 20. In FIG. 3B through FIG. 3D, a cable 26 is retracted within stylus 20, such as by way of a connected angulation screw 32 on handle 28. Retracting a cable 26 causes stylus 20 to angulate out of window 18 in the direction of the retracted cable 26. For example, a stylus 20 having two or more cables 26 can have its distal tip angulated in the direction of any of the cables 26 by retracting one or more cable 26. The degree of angulation can be varied between about 0 degrees and 90 degrees relative to the axis of the cannula 16 by adjusting the amount of retraction of a cable 26 at a connected angulation screw 32. In various embodiments, stylus 20 can be repositioned within cannula 16 by adjusting extension knob 30, such as in FIG. 3D. The combination of angulation control and positional control of stylus 20 relative to cannula 16 enables device 10 to accurately aim needle 22 towards the fossa ovalis. In certain embodiments, device 10 can be aimed at a specific location of the fossa ovalis. The fossa ovalis can be divided into quadrants, wherein a puncture in each quadrant is advantageous for a specific procedure. For example, device 10 can be aimed to puncture slightly superior, posterior, and 3.5 cm-4.5 cm above the mitral valve for typical Mitraclip devices, and is further configured to puncture posterior and slightly inferior within the fossa ovalis for typical left atrial appendage occlusion devices.

In various embodiments, device 10 can further comprise one or more modifications to enhance its performance. For example, in some embodiments device 10 can include one or more additional instruments positioned within a lumen of stylus 20, such as an endoscope assembly, an ultrasound transducer, a temperature sensor, an oxygen probe, a flow sensor, a cauterizer, and the like. In another example, device 10 can comprise one or more radiopaque or echo-bright markers positioned on cannula 16, stylus 20, or both. The markers enable the position of device 10 to be monitored via fluoroscopy or echocardiography, and can be placed at or near structures of interest, including but not limited to the distal tips of cannula 16 and stylus 20 and the at least one window 18.

Figure 4B:
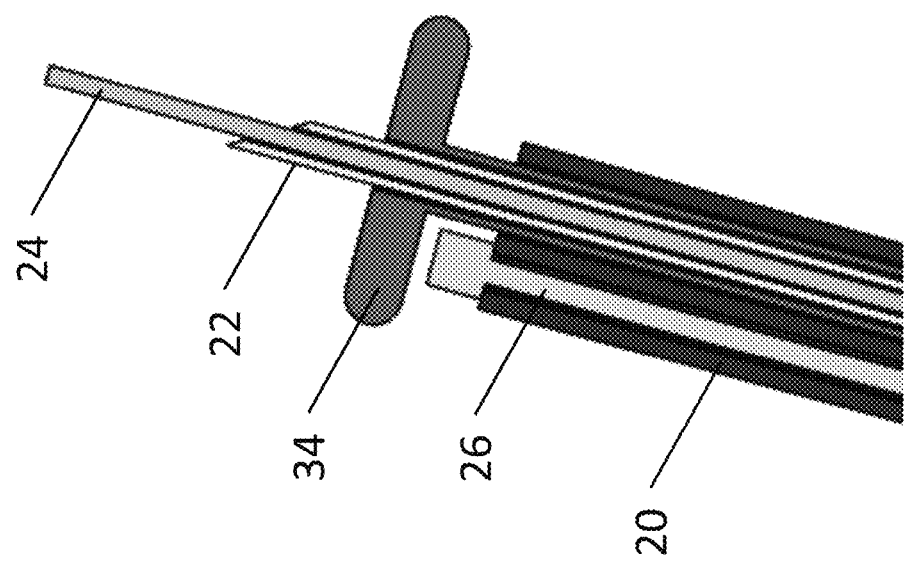
FIG. 4B depicts a side cross-sectional view of the device.
Figure 4A:
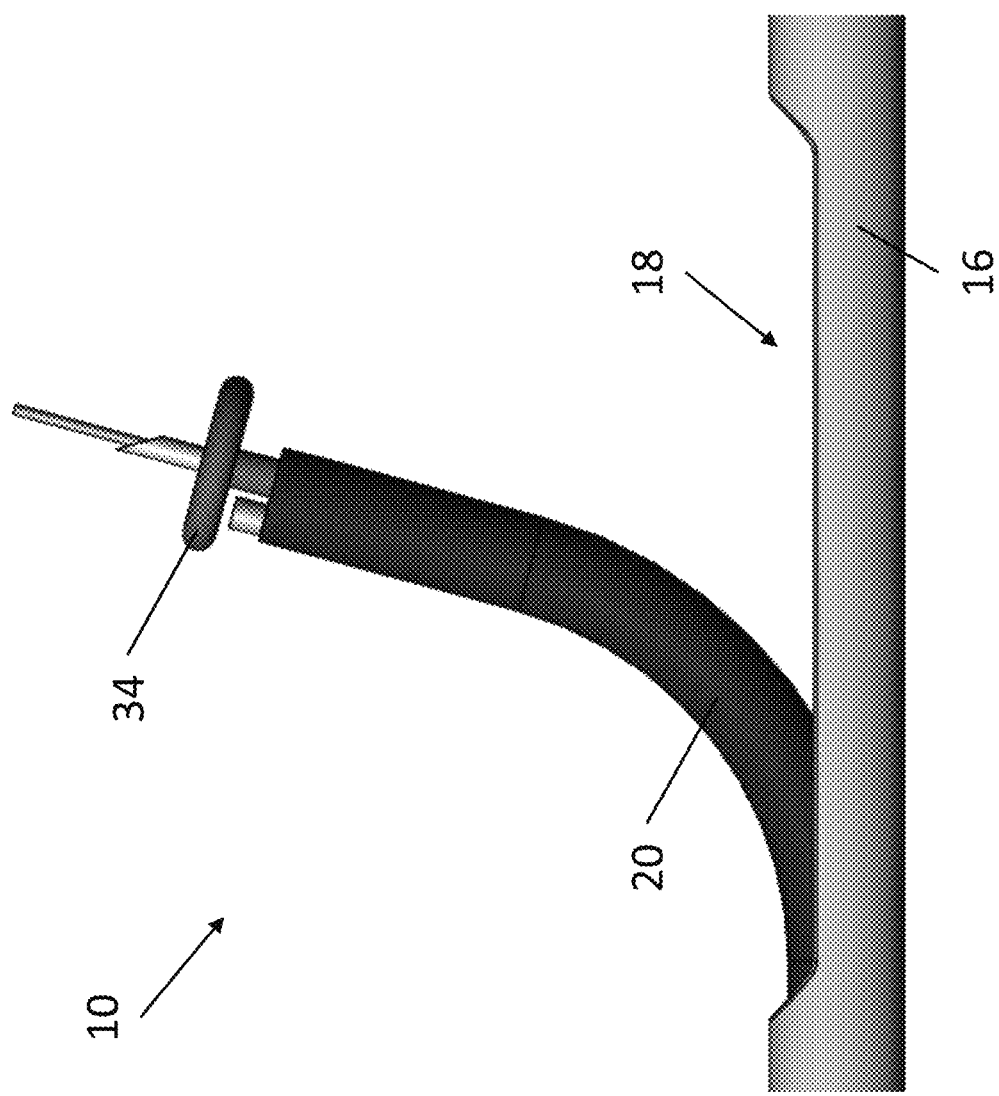
FIG. 4A depicts an exemplary transseptal puncture device having an atraumatic support.
Figure 5:
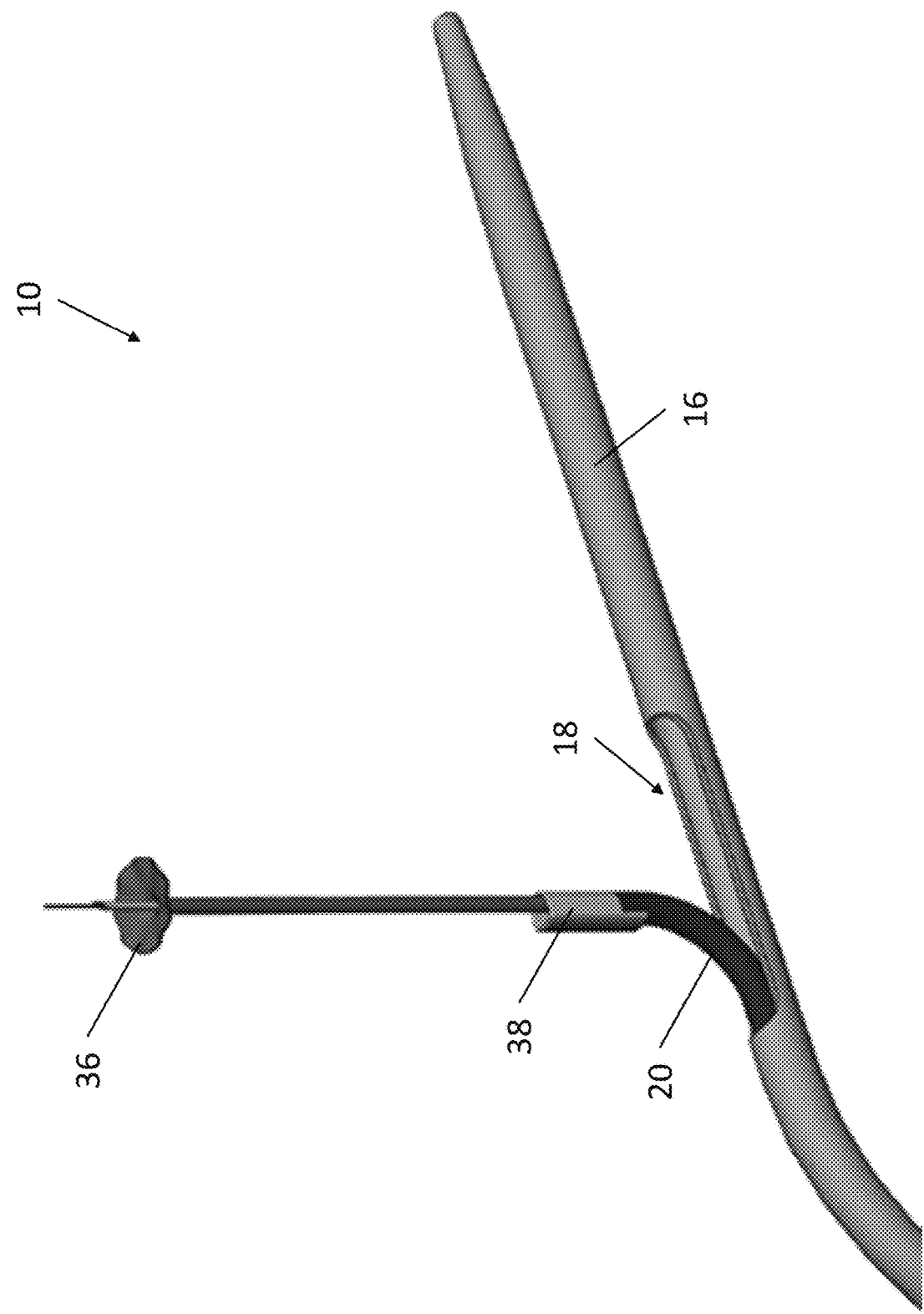
FIG. 5 depicts another exemplary transseptal puncture device having an atraumatic support.
Figure 6A:
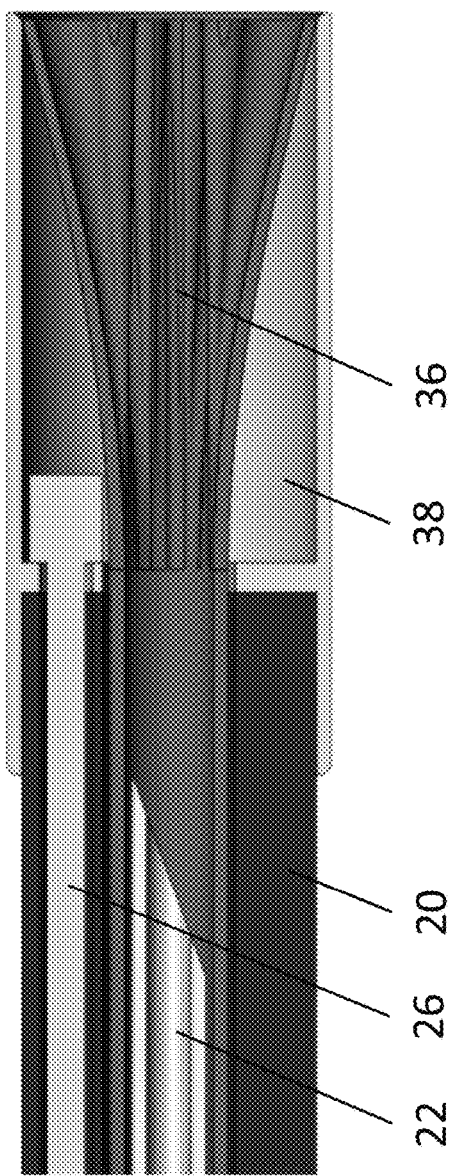
FIG. 6A through FIG. 6D depict the storage and deployment of an atraumatic support of an exemplary transseptal puncture device.
Figure 6B:
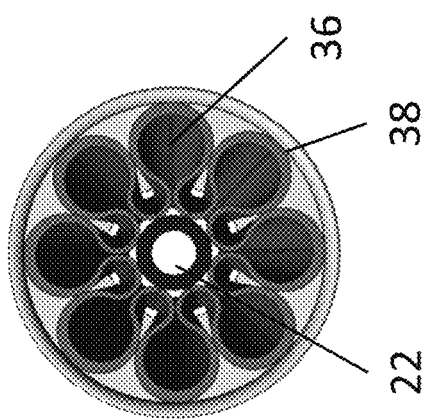
Figure 6D:
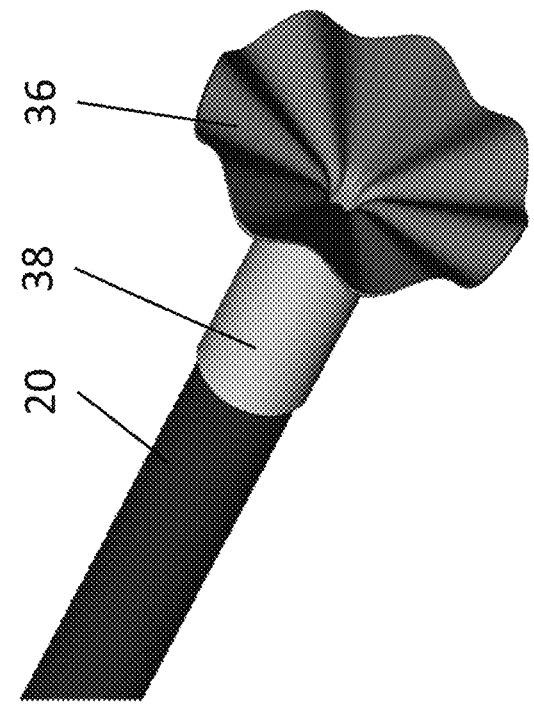
Figure 6C:
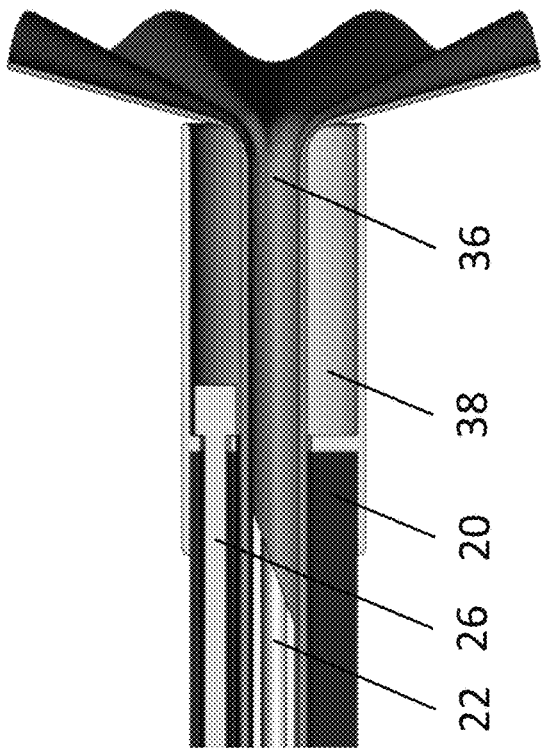

In some embodiments, device 10 can include an atraumatic support 34 as shown in FIG. 4A and FIG. 4B. Atraumatic support 34 has an elongate tubular shape and can fit within the first lumen of stylus 20 around needle 22. Atraumatic support 34 further comprises a blunt tip at its distal end. In some embodiments the blunt tip includes an inflatable balloon. In still another embodiment, the blunt tip is a flattened end-effector. In still yet another embodiment, the blunt tip is a ring-like end-effector. The blunt tip of atraumatic support 34 provides the distal end of stylus 20 with a greater surface area to minimize injury and increase stability by providing uniform pressure when placed against a tissue surface, such as the fossa ovalis. In FIG. 5, device 10 is depicted having atraumatic support 36 with a bell-tip configured to be collapsible and withdrawable into a sheath 38 attached to the distal end of stylus 20. Similar to atraumatic support 34, atraumatic support 36 is generally configured to increase the surface area of stylus 20 that is in contact with the fossa ovalis tissue (prior to puncturing the fossa ovalis) to decrease the pressure on the tissue and to reduce or prevent the likelihood of premature puncture and/or damage. A collapsible design enables device 10 to support a wide bell-tip, such as width of between about 8 mm and 15 mm, within the confines of cannula 16. Referring now to FIG. 6A through FIG. 6D, the geometry of atraumatic support 36 is shown in detail. Atraumatic support 36 comprises a bell-tip at its distal end having a plurality of undulating folds. Withdrawing atraumatic support 36 into sheath 38 causes the bell-tip to bunch together in a controlled manner to fit within sheath 38 while maintaining a space for the passage of needle 22. Needle 22 is thereby capable of being extended and retracted past the bell-tip of atraumatic support 36 regardless of whether the bell-tip is in a collapsed or an open configuration.

Figure 7B:
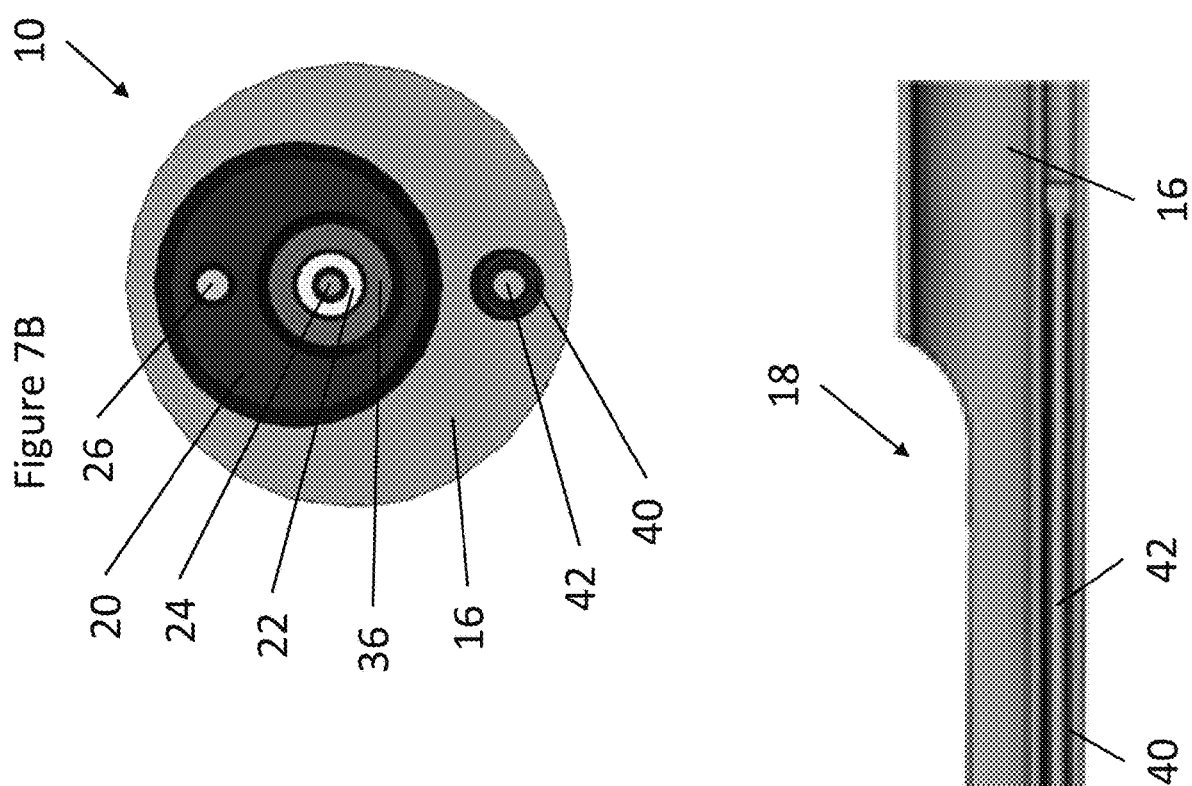
FIG. 7A and FIG. 7B depict an exemplary transseptal puncture device having a cannula-stiffening component.
Figure 7A:
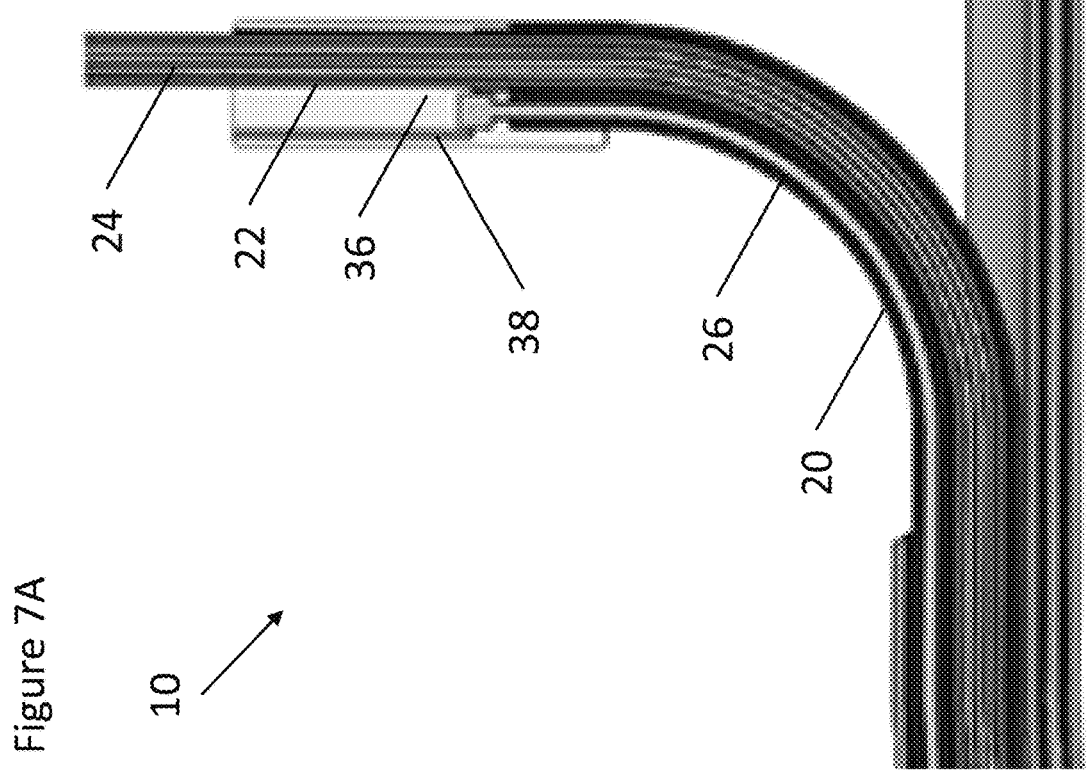

In some embodiments, device 10 can include a stiffening element configured to modify the rigidity of a section of device 10. Increasing the stiffness of a section of device 10, such as a section of cannula 16 comprising at least one window 18, provides device 10 with a stable backbone against which an extended stylus 20 and needle 22 can push against to penetrate a tissue. Referring now to FIG. 7A and FIG. 7B, device 10 is depicted with a stiffening element comprising spine 40 and cable 42. Spine 40 is positioned within a second lumen of cannula 16 and extends to at least the location of the at least one window 18. Spine 40 is constructed such that it is flexible when loose and stiff when compacted. For example, in one embodiment, spine 40 is an elongate tubular member constructed from a compressible polymer. In other embodiments, spine 40 is made from a long chain of interlocking segments or from a series of hollow tubules loosely positioned next to one another, constructed from either a plastic or a metal. Cable 42 runs through the entire length of spine 40 and comprises a tip at its distal end that is wider than spine 40. Retracting cable 42 presses its tip against the distal end of spine 40, thereby compacting the entire length of spine 40 and stiffening spine 40 and the length of cannula 16 that spine 40 resides in. Extending cable 42 relieves the pressure that its tip exerts on the distal end of spine 40, which relaxes spine 40 and the length of cannula 16 that spine 40 resides in.

Figure 8A:
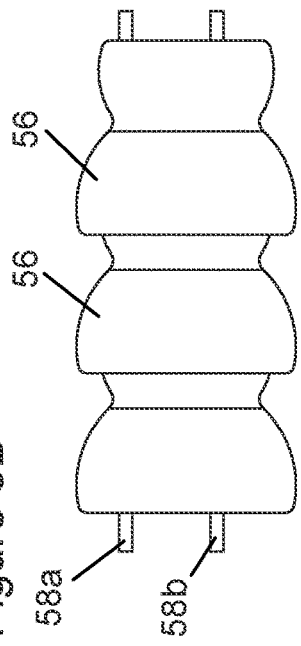
FIG. 8A through FIG. 8D depict an exemplary segmented transseptal puncture device.
Figure 8B:
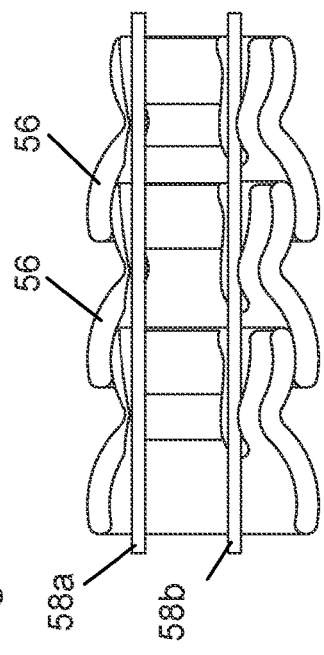
Figure 8C:
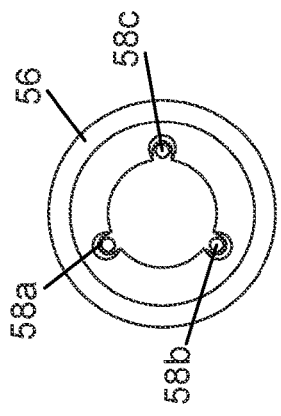
Figure 8D:
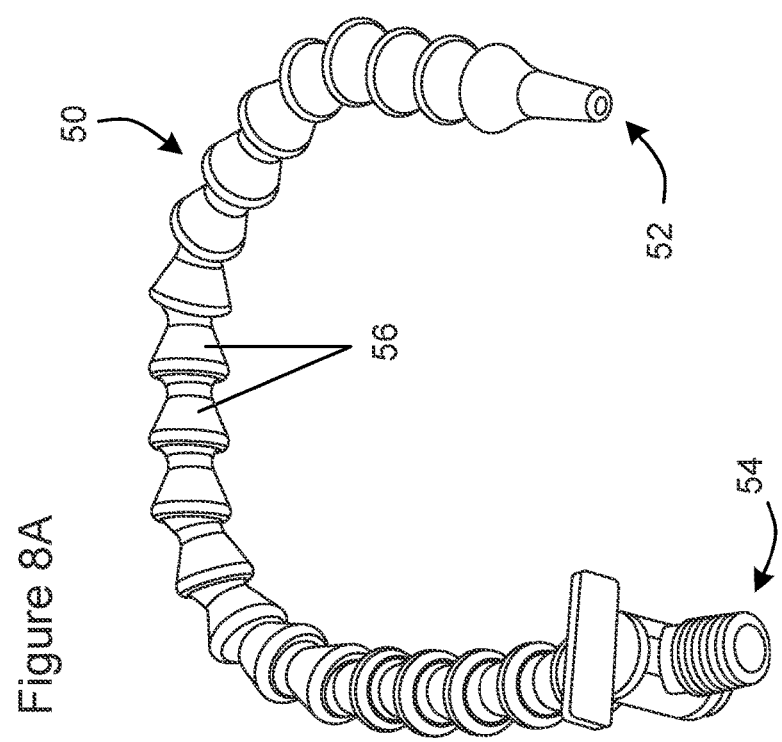

Referring now to FIG. 8A through FIG. 8C, an exemplary segmented transseptal puncture device 50 is depicted. Device 50 comprises a plurality of interlocking segments 56 between a distal end 52 and a proximal end 54. Interlocking segments 56 can have any suitable construction to form an elongate, flexible member. For example, in some embodiments, tach interlocking segment 56 comprises a first end having a small hollow spherical shape and a second end having a large hollow spherical shape, such that the first end of one interlocking segment 56 fits flush within the second end of another interlocking segment 56 to form a ball joint. A plurality of interlocking segments 56 connected in this manner thereby forms an elongate, articulating series of ball joints. In other examples, interlocking segments 56 can form a gooseneck member, a snake chain member, and the like. Device 50 further comprises at least a first cable 58a, a second cable 58b, and a third cable 58c running throughout its entire length, each cable 58a, 58b, and 58c being arranged equidistantly from each other in a radial pattern. Each cable 58a, 58b, and 58c is attached to the distal-most interlocking segment 56, such that retracting any one or two of cable 58a, 58b, or 58c causes distal end 52 of device 50 to curl in the direction of the retracted cables. Retracting all of the cables 58a, 58b, and 58c with the same amount of force causes device 50 to stiffen and retain its instant shape.

Referring now to FIG. 9A through FIG. 9D, two exemplary configurations of device 50 are shown. In FIG. 9A and FIG. 9B, device 50 fits within the lumen of a cannula 62 and comprises a needle 60 running throughout its hollow interior. In FIG. 9C and FIG. 9D, device 50 fits within a first lumen of cannula 62 and needle 60 fits within a second lumen of cannula 62. In this configuration, the hollow interior of device 50 can be used to house an additional instrument, such as an endoscope assembly, an ultrasound transducer, any number of sensor probes (including temperature probes, oxygen sensors, flow sensors), and the like.

Referring now to FIG. 10A through FIG. 10D, an exemplary expandable transseptal puncture device 70 is depicted. Device 70 has a distal end 71, a proximal end 72, and a cannula 74 running throughout. Device 70 has a plurality of slits 75 positioned near its distal end 71 uniformly distributed around cannula 74, such that a plurality of arms 76 are formed between adjacent slits 75. Compressing cannula 74 on either side of the plurality of slits 75 expands the arms 76 outwards, revealing catheter section 78 running through cannula 74. Catheter section 78 has a rigid construction, formed by either a hard plastic or a metal, and permits at least the distal end 71 of cannula 74 to advance proximally over catheter section 78 to achieve expansion of arms 76. In certain embodiments, the distal end 71 of cannula 74 is manipulated using one or more pull cables running through the length of device 70. For example, the one or more pull cables can be equally retracted to expand each arm 76 uniformly and to form equally sized openings between each arm 76. In another example, the one or more pull cables can be selectively retracted, such that pull cables subjected to more tension cause greater expansion in the arms 76 closest to those pull cables, varying the geometry of the opening between each arm 76. Expanded arms 76 provide clearance for the extension of stylet 80 out of catheter section 78, and also for the extension of hollow needle 82 out of stylet 80 and any desired guidewires out of hollow needle 82.

As described above, device 70 has a relaxed state with a thin profile (FIG. 10A) and an expanded state (FIG. 10B). The relaxed state permits device 70 to be guided into the right atrium of a patient's heart such that the distal end of device 70 rests in the patient's super vena cava. In the expanded state, the plurality of arms 76 are configured to selectively press against the wall of the right atrium adjacent to the fossa ovalis to enhance stability (e.g., lateral stability). Device 70 thereby provides at least two stable platforms for transseptal puncture using stylet 80: the plurality of arms 76 pressing directly against the heart tissue, and the catheter section 78 suspended between the plurality of arms 76. Selective retraction of pull cables in device 70 to non-uniformly expand device 70 can be desirable in certain situations. For example, device 70 can be expanded such that the arms 76 adjacent to stylet 80 are greatly expanded to provide a larger clearance for fossa ovalis access, while the arms 76 behind stylet 80 can be expanded to a lesser degree to increase stability in the area immediately behind stylet 80.

Referring now to FIG. 11A through FIG. 11H, further configurations of device 70 are depicted. While exemplary devices 70 are depicted with three and six arms 76, it should be understood that device 70 can have any suitable number of arms 76, such as between about three and ten arms. In certain embodiments, the plurality of arms 76 can each be linked by one or more band 86, as shown in FIG. 11E and FIG. 11F. By linking each arm 76 to its adjacent arm 76, band 86 increases the stability of device 70 by mitigating lateral motion of each arm 76 and prevents injury from excessive expansion of arms 76. In certain embodiments, the plurality of arms 76 can be encased in covering 88, as shown in FIG. 11G and FIG. 11H. Covering 88 is elastic and can be waterproof to smoothly guide device 70 in a relaxed state and to provide a greater surface area in an expanded state that spreads out pressure and decrease trauma. Covering 88 also provides the same benefits of band 86, in that covering 88 mitigates lateral motion and excessive expansion of arms 76 to improve stability. In FIG. 11H, stylet 80 and needle 82 are depicted as capable of piercing through covering 88 to access and puncture the fossa ovalis.

Referring now to FIG. 12A and FIG. 12B, an exemplary device 70 is depicted having loop guide 89. Loop guide 89 provides additional stability by linking an extended stylus 80 to an expanded arm 76. In some embodiments, loop guide 89 is attached to the distal end of stylus 80, such that after expanding the plurality of arms 76, stylus 80 can be extended along an expanded arm 76 as loop guide 89 slides over the expanded arm 76. In other embodiments, loop guide 89 is welded to both the distal end of stylus 80 and to an expanded arm 76, such that the expanding action of arm 76 simultaneously extends stylus 80 and curves stylus 80 towards a fossa ovalis.

Figure 13A:
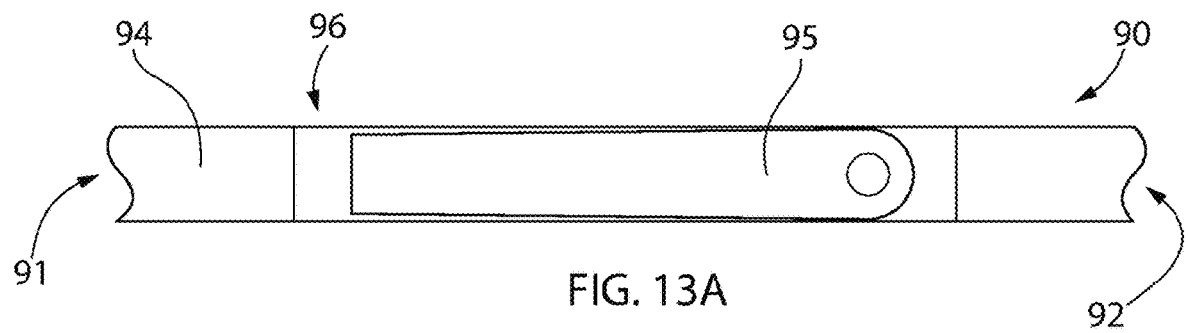
FIG. 13A through FIG. 13C depict exemplary hinged transseptal puncture devices.
Figure 13B:
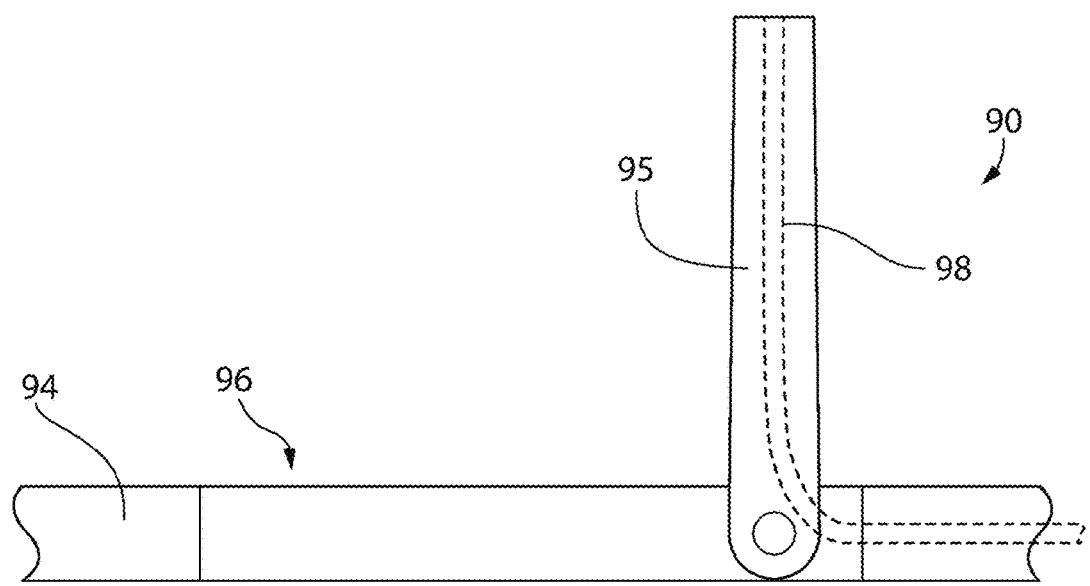
Figure 13C:
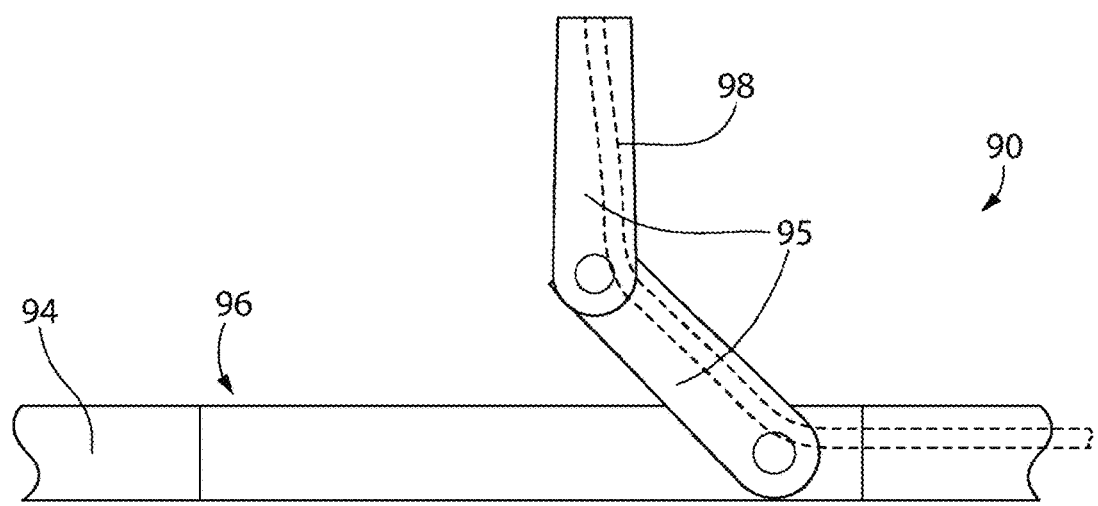

Referring now to FIG. 13A through FIG. 13C, exemplary hinged transseptal puncture devices 90 are depicted. Device 90 has a distal end 91, a proximal end 92, and a cannula 94 running throughout. Device 90 has a hinged arm 95 near its distal end 91, the hinged arm 95 resting within cannula 94 adjacent to window 96. Hinged arm 95 is attached to the distal end of stylus 98, such that rotating hinged arm 95 out of window 96 extends stylus 98 out of cannula 94 to face towards a fossa ovalis. While exemplary embodiments of device 90 are shown with one and two points of articulation in FIG. 13B and FIG. 13C, respectively, it should be understood that hinged arm 95 can have any suitable number of points of articulation, such as between about one and ten. Hinged arm 95 can be rotated using any suitable means, including but not limited to one or more pull cables, one or more servomotors, one or more hydraulic pistons, and the like.

The various components of the present invention described above can be constructed using any suitable method known in the art. The method of making may vary depending on the materials used. For example, components substantially comprising a metal may be milled from a larger block of metal or may be cast from molten metal. Likewise, components substantially comprising a plastic or polymer may be milled from a larger block, cast, or injection molded. In some embodiments, the devices may be made using 3D printing or other additive manufacturing techniques commonly used in the art.

Methods of Transseptal Puncture

Figure 14:
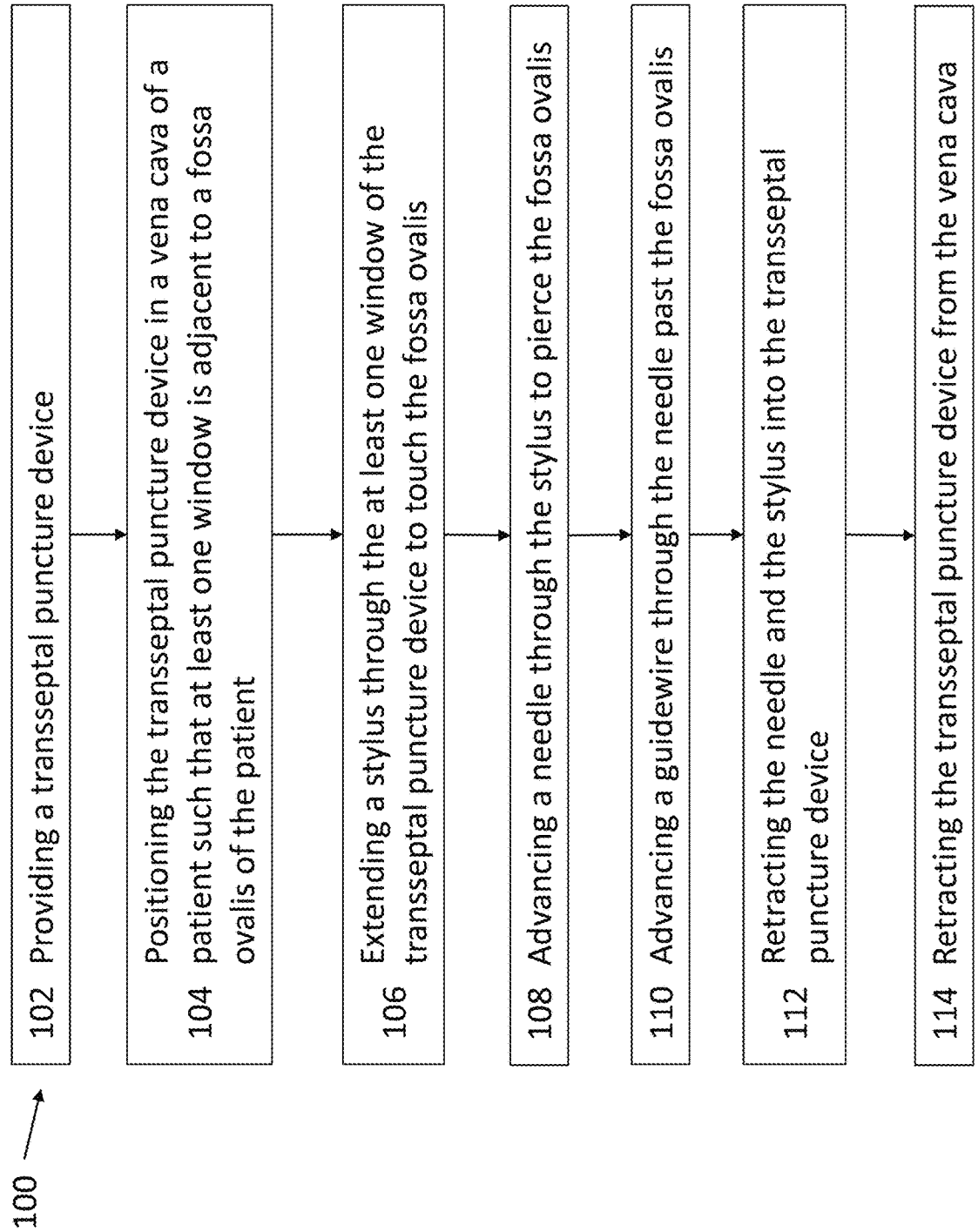
FIG. 14 is a flowchart of an exemplary method of puncturing the fossa ovalis of a patient.

The present invention further includes methods of using the transseptal puncture devices of the present invention. Referring now to FIG. 14, an exemplary method 100 is depicted. Method 100 begins with step 102, wherein a transseptal puncture device of the present invention is presented. In step 104, the transseptal puncture device is positioned within the vena cava of a patient such that the at least one window of the transseptal puncture device is adjacent to a fossa ovalis of the patient. In step 106, a stylus is extended through the at least one window of the transseptal puncture device to touch the fossa ovalis. In step 108, a needle is advanced through the stylus to pierce the fossa ovalis. In step 110, a guidewire is advanced through the needle past the fossa ovalis. In step 112, the needle and the stylus are retracted into the transseptal puncture device. In step 114, the transseptal puncture device is retracted from the vena cava, leaving behind the guidewire.

The transseptal puncture device can be inserted into the vena cava using any suitable method. For example, a typical method places a catheter in the femoral vein according to typical procedures, such as under fluoroscopy, by puncturing the femoral vein with a hollow puncture device (needle) and placing a guidewire (e.g., a 0.035" guidewire) into the femoral vein. The device is inserted over the guidewire to the level of the superior vena cava. The distal end of the cannula can lie above the superior vena cava (e.g., at the level of the innominate branch) with sufficient length to allow cranial or caudal manipulation of the cannula to ensure that the opening of the at least one window is generally aligned and facing the fossa ovalis. In some embodiments, the position and the placement of the at least one window (i.e. next to the fossa ovalis) can be confirmed on echocardiography and fluoroscopy. The proximal end of the device, including the handle and adjustment knobs, is externalized at the groin.

In certain embodiments, the cannula can be stiffened prior to deploying the stylus, such as by retracting a cable to compact a spine embedded in the cannula. Stiffening the cannula provides a deployed stylus with a rigid and stable backbone to push against to penetrate the fossa ovalis. In certain embodiments, a transseptal puncture device having an atraumatic support can be deployed with the stylus to minimize injury and to provide additional support to fossa ovalis penetration. Pressing an atraumatic support against the fossa ovalis spreads out the pressure against the fossa ovalis and provides a guided path for the needle from the puncture device directly to the fossa ovalis.

In certain embodiments, the needle can be aimed at a specific region of the fossa ovalis for puncture. As described elsewhere herein, the fossa ovalis can be divided into quadrants, wherein a puncture in each quadrant is advantageous for a specific procedure. The needle can thereby be aimed to puncture slightly superior, posterior, and 3.5 cm-4.5 cm above the mitral valve for a Mitraclip devices, or to puncture posterior and slightly inferior within the fossa ovalis for typical left atrial appendage occlusion devices. After successful puncture and insertion of a guidewire, the transseptal puncture device can be completely removed to make way for any suitable instrument or device to be guided into the left atrium of the heart to perform a desired procedure, such as atrial fibrillation ablation, left atrial appendage closure, and valve replacements.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out exemplary embodiments of the present invention, and are not to be construed as limiting in any way the remainder of the disclosure.

Example 1

Demonstration of Model Fossa Ovalis Puncture

Figure 15E:
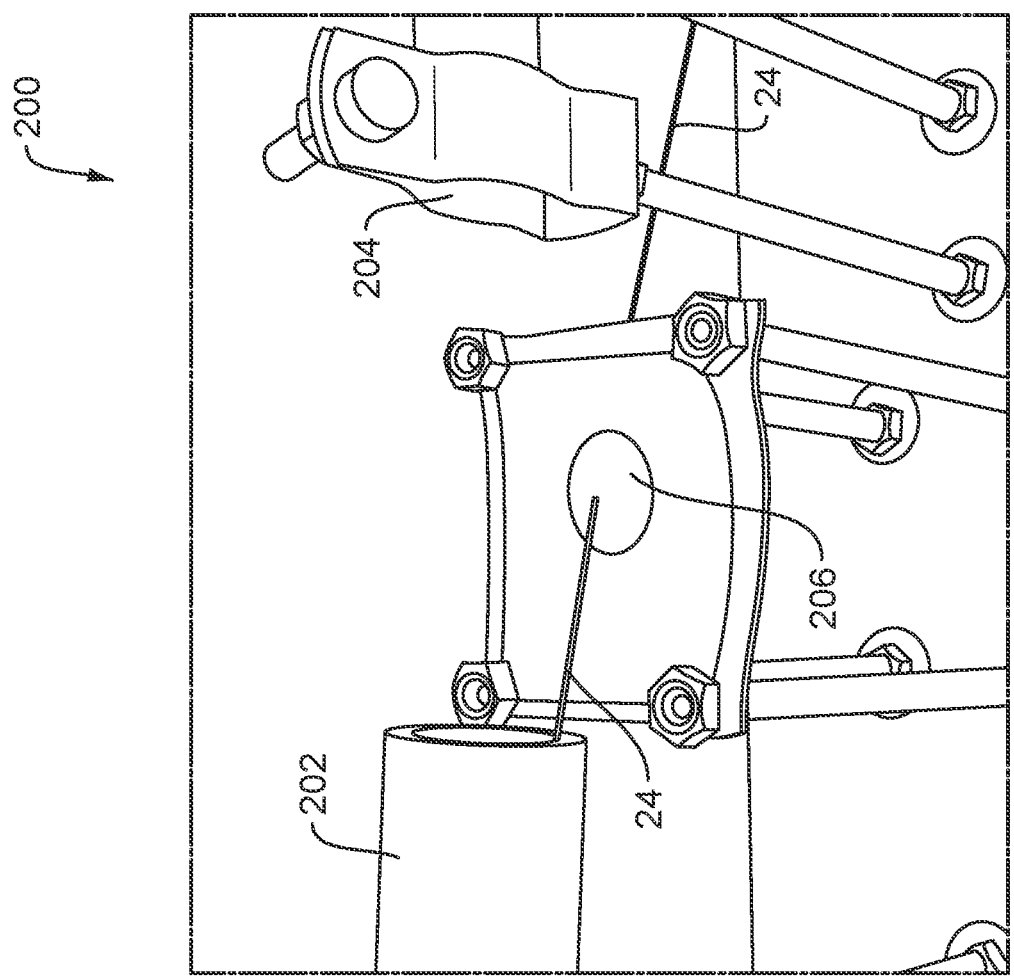

FIG. 15A through FIG. 15E depict the sequence of a model fossa ovalis penetration using a prototype transseptal puncture device 10. The depicted experimental setup 200 includes tubing representing the inferior vena cava 202, tubing representing the superior vena cava 204, a gap inbetween inferior vena cava 202 and superior vena cava 204 representing a portion of the right atrium space, and a suspended membrane representing the fossa ovalis 206. In FIG. 15A, a prototype device 10 has been advanced through the inferior vena cava 202 to position a window of cannula 16 adjacent to the fossa ovalis 206. A length of cannula 16 rests within the superior vena cava 204 to enhance stability. Deployment of stylus 20 has begun, causing stylus 20 to angulate out of the window of cannula 16. In FIG. 15B, the fully deployed stylus 20 is pressed against the fossa ovalis 206, causing tenting to be visible. In FIG. 15C, the fossa ovalis 206 has been punctured by a needle (not visible), permitting guidewire 24 to be advanced through the fossa ovalis 206 and into the model left atrium space. In FIG. 15D, access to the model left atrium space has been established with a sufficient length of guidewire 24, and device 10 can be withdrawn. Withdrawal of stylus 20 has begun, causing stylus 20 to angulate into the window of cannula 16. In FIG.

15E, device 10 has been fully withdrawn from the inferior vena cava 202 and superior vena cava 204, leaving behind only guidewire 24 to guide any desired instrument.

Safety is generally compared by incidence of puncture of an unintended structure (e.g., success=zero incidence). Duration of time to perform transseptal puncture is generally the duration of time between the prototype and the conventional transseptal puncture devices and the combination of accuracy. The duration of time is generally quantified and compared using an accuracy-speed tradeoff model. Thus, the method of using the device to puncture the fossa ovalis generally increases safety by increasing precision of the puncture location and decreases procedure duration compared to typical devices.

In some procedures, comparisons with typical devices are determined by endpoints, including: (1) duration of time to perform transseptal puncture and insert pigtail wire; (2) accuracy of the prototype compared to conventional technology (expected vs. observed puncture location); (3) safety of the prototype compared to conventional technology (rate/consequences of adverse events); and (4) the combination of speed and accuracy (i.e. learning curve). Furthermore, the devices and methods of using the devices may be further compared for novice physicians (e.g., performed less than approximately 20 procedures) and skilled physicians (e.g., performed more than approximately 20 procedures).

The devices have also been tested in the static heart in vitro, indicating that the device will fit appropriately within the vena cava (superior and inferior) and that it can be advanced to the level of the fossa ovalis. The device also allows for delivery of left atrial appendage closure or ablation devices, and percutaneous delivery of prosthetic valves to the aortic and mitral sites. Furthermore, the device and method allows for a radiofrequency generating tip for use in an electrophysiology (EP) lab, for example.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method, comprising:
   inserting a shaft having a deflectable stylus coupled thereto into a heart such that a distal end portion of the stylus is disposed within a right atrium of a heart;
   deflecting the stylus such that the distal end portion of the stylus points away from a central axis of the shaft and towards the septum of the heart;
   extending an atraumatic support (1) having an end effector at its distal end, and (2) that is disposed at least partially within the stylus, distally from a distal end portion of the stylus such that the end effector contacts the septum; and
   with the end effector in contact with the septum, extending a puncture member that is slidably disposed within the atraumatic support distally from the end effector such that the puncture member pierces the septum.

2. The method of claim 1, wherein the extending the puncture member distally from the atraumatic support includes extending the puncture member distally along a longitudinal axis that is substantially perpendicular to a longitudinal axis of the shaft.

3. The method of claim 1, further comprising:
   visualizing from outside the patient a radiopaque or echo-bright marker that is disposed at the shaft, the atraumatic support, the end effector, or the stylus, and within the heart of the patient.

4. The method of claim 1, wherein the inserting the shaft includes slidably advancing the shaft about a guidewire.

5. The method of claim 1, wherein the inserting the shaft includes inserting the shaft into an inferior vena cava (IVC) of the heart and a superior vena cava (SVC) of the heart, and wherein the extending the atraumatic support occurs with the shaft spanning the IVC and the SVC.

6. The method of claim 1, wherein the stylus is slidably coupled to the shaft.

7. The method of claim 1, wherein the extending the puncture member distally from the atraumatic support includes extending the puncture member distally along an longitudinal axis that is between about 0 degrees and about 90 degrees relative to a longitudinal axis of the shaft.

8. The method of claim 1, wherein the extending the puncture member such that the puncture member pierces the septum includes extending the puncture member into a left atrium of the heart, the method further comprising:
   with the puncture member disposed in the left atrium, extending distally a guide wire from within a lumen defined by the puncture member from the puncture member and into the left atrium.

9. The method of claim 8, further comprising:
   with the guide wire disposed in the left atrium, withdrawing proximally the puncture member from the left atrium and into the atraumatic support such that a distal end of the puncture member is disposed within the atraumatic support.

10. The method of claim 1, wherein the extending the atraumatic support distally from the stylus towards and into contact with the septum includes tenting the septum with the end effector such that a fossa ovalis of the tented septum is urged into a left atrium of the heart.

11. The method of claim 10, wherein the extending the puncture member such that the puncture member pierces the septum includes piercing the septum with the septum tented by the end effector.

12. The method of claim 1, wherein the extending the puncture member such that the puncture member pierces the septum includes piercing a fossa ovalis of the heart.

13. The method of claim 12, wherein the extending the atraumatic support distally from the distal end portion of the stylus includes extending the end effector from a lumen defined by the stylus such that the end effector expands in cross-sectional area as it exits the lumen.

14. The method of claim 13, wherein the end effector expands as it exits the lumen from a diameter of between about 5 mm and about 7 mm to a diameter of between about 8 mm and about 15 mm.

15. The method of claim 13, wherein the end effector expands as it exits the lumen at least about three times its diameter when the end effector was disposed within the lumen.

16. The method of claim 1, wherein prior to the extending the atraumatic support distally from the distal end portion of the stylus, the end effector of the atraumatic support is disposed within a lumen defined by the stylus.

17. The method of claim 1, further comprising:
   visualizing from outside the patient a radiopaque or echo-bright marker disposed within the heart of the patient.

18. The method of claim 1, wherein the end effector has a cross-sectional area greater than a cross-sectional area of the distal end portion of the stylus.

19. The method of claim 1, wherein the end effector includes a bell shape.

20. The method of claim 1, wherein the end effector has a flat distal end surface.

21. The method of claim 1, wherein the extending the atraumatic support distally from the distal end portion of the stylus includes extending the atraumatic support distally from a terminal distal end of the stylus.

22. The method of claim 1, wherein the extending the atraumatic support includes extending the atraumatic support through a window defined by the shaft proximal to a distal end of the shaft.

23. A method, comprising:
with a deflectable stylus disposed within a right atrium of a heart of a patient, extending an atraumatic support (1) having an end effector at its distal end, and (2) that is disposed at least partially within the stylus, through a lumen defined by the stylus and distally from a distal end portion of the stylus such that the end effector (1) expands in cross-sectional area as it exits the lumen, and (2) contacts the septum; and
with the end effector in contact with the septum, extending a puncture member that is slidably disposed within the atraumatic support distally from the end effector such that the puncture member pierces a fossa ovalis of the septum.

24. The method of claim 23, further comprising:
visualizing from outside the patient a radiopaque or echo-bright marker that is disposed at the atraumatic support, the end effector, or the stylus, and within the heart of the patient.

25. The method of claim 23, wherein the extending the puncture member such that the puncture member pierces the septum includes extending the puncture member into a left atrium of the heart, the method further comprising:
with the puncture member disposed in the left atrium, extending distally a guide wire from within a lumen defined by the puncture member from the puncture member and into the left atrium.

26. The method of claim 25, further comprising:
with the guide wire disposed in the left atrium, withdrawing proximally the puncture member from the left atrium and into the atraumatic support such that a distal end of the puncture member is disposed within the atraumatic support.

27. The method of claim 23, wherein the extending the atraumatic support distally from the stylus and into contact with the septum includes tenting the septum with the end effector such that a fossa ovalis of the tented septum is urged into a left atrium of the heart.

28. The method of claim 23, wherein the end effector expands as it exits the lumen from a diameter of between about 5 mm and about 7 mm to a diameter of between about 8 mm and about 15 mm.

29. The method of claim 23, wherein the end effector expands as it exits the lumen at least about three times its diameter when the end effector was disposed within the lumen.

30. The method of claim 23, wherein the extending the puncture member such that the puncture member pierces the septum includes piercing the septum with the septum tented by the end effector.

* * * * *